United States Patent [19]
Haugwitz et al.

[11] Patent Number: 4,681,886
[45] Date of Patent: Jul. 21, 1987

[54] SUBSTITUTED 4-PHENOXY OR 4-PHENYLTHIO PROLINES

[75] Inventors: Rudiger D. Haugwitz, Titusville; Peter W. Sprague, Pennington, both of N.J.

[73] Assignee: E. R. Squibb & Sons, Inc., Princeton, N.J.

[21] Appl. No.: 488,491

[22] Filed: Apr. 25, 1983

Related U.S. Application Data

[63] Continuation-in-part of Ser. No. 373,570, Apr. 30, 1982, abandoned.

[51] Int. Cl.[4] .................. A61K 31/505; A61K 31/54; C07D 403/12; C07D 417/12
[52] U.S. Cl. .................................... 514/259; 514/222; 544/12; 544/13; 544/244; 544/284; 544/287; 544/288; 544/289
[58] Field of Search ................ 424/251; 544/244, 284, 544/287, 288, 289; 514/259

[56] References Cited

U.S. PATENT DOCUMENTS

| 3,040,042 | 6/1962 | Yale et al. | 424/247 |
|---|---|---|---|
| 4,105,776 | 8/1978 | Ondetti et al. | 424/274 |
| 4,168,267 | 9/1979 | Petrillo | 424/274 |
| 4,217,347 | 8/1980 | Horovitz et al. | 424/246 |
| 4,316,906 | 2/1982 | Ondetti et al. | 424/274 |
| 4,337,201 | 6/1982 | Petrillo | 548/413 |
| 4,374,829 | 2/1983 | Harris | 424/177 |
| 4,431,644 | 2/1984 | Smith et al. | 424/246 |
| 4,431,645 | 2/1984 | Smith et al. | 424/246 |

FOREIGN PATENT DOCUMENTS

| 879158 | 10/1979 | Belgium . |
|---|---|---|
| 12401 | 6/1980 | European Pat. Off. . |
| 18549 | 11/1980 | European Pat. Off. . |
| 88350 | 1/1983 | European Pat. Off. . |
| 2045249 | 10/1980 | United Kingdom . |

OTHER PUBLICATIONS

Tanabe, Abstracts of Japanese Application 5151-555, published Nov. 1980.

Primary Examiner—Glennon H. Hollrah
Assistant Examiner—James H. Turnipseed
Attorney, Agent, or Firm—Lawrence S. Levinson; Stephen B. Davis

[57] ABSTRACT

This invention is directed to substituted 4-phenoxy and 4-phenylthio prolines of the formula

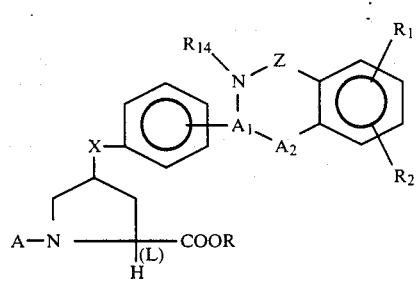

which possess useful hypotensive activity.

17 Claims, No Drawings

SUBSTITUTED 4-PHENOXY OR 4-PHENYLTHIO PROLINES

RELATED APPLICATION

This application is a continuation-in-part of U.S. Ser. No. 373,570 filed Apr. 30, 1982, now abandoned.

BACKGROUND OF THE INVENTION

Ondetti et al. in U.S. Pat. No. 4,105,776 disclose that various mercaptoacyl derivatives of proline, hydroxy substituted proline, and alkyl substituted proline are useful hypotensive agents due to their angiotensin converting enzyme inhibition activity.

Ondetti et al. in U.S. Pat. No. 4,316,906 disclose that mercaptoacyl derivatives of various ether and thioether substituted prolines are also useful hypotensive agents due to their angiotensin converting enzyme inhibition activity.

Horovitz et al. in U.S. Pat. No. 4,217,347 disclose reducing blood pressure by administering a composition including a diuretic and the mercaptoacyl proline compounds taught by Ondetti et al. in U.S. Pat. No. 4,105,776.

Yoshitomi in Belgian Pat. No. 879,158 disclose chlorosulfamoylbenzoylthiopropionyl prolines and thiazolidines as possessing diuretic and hypotensive activity.

Tanabe in European Patent Application No. 18,549 disclose angiotensin converting enzyme inhibitors having a carboxyethylcarbamoyl group attached to the N-atom of tetrahydroisoquinoline carboxylic acid and this same sidechain coupled to the N-atom of proline in Japanese Application No. 5151-555.

Patchett et al. in European Patent Application No. 12,401 and U.S. Pat. No. 4,374,829 disclose that various carboxyalkyl dipeptides are angiotensin converting enzyme inhibitors.

Petrillo in U.S. Pat. Nos. 4,168,267 and 4,337,201 disclose that various phosphinylalkanoyl prolines, substituted prolines, and their esters are angiotensin converting enzyme inhibitors.

SUMMARY OF THE INVENTION

This invention relates to new substituted 4-phenoxy or 4-phenylthio prolines and salts thereof of the formula (I)

wherein
X is oxygen or sulfur.
$-A_1-A_2-$ is $-CH-NH-$ or $-C=N-$.
A is $$R_4-S-CH_2-\overset{R_3}{\underset{|}{CH}}-\overset{O}{\underset{\|}{C}}-,\ R_8OOC-(CH_2)_2-\overset{R_7}{\underset{|}{N}}-\overset{O}{\underset{\|}{C}}-,$$

-continued
$$R_9OOC-\overset{R_{10}}{\underset{|}{CH}}-NH-\overset{R_{11}}{\underset{|}{CH}}-\overset{O}{\underset{\|}{C}}-,\ \text{or}\ R_{12}-\overset{O}{\underset{\underset{OR_{13}}{|}}{\overset{\|}{P}}}-CH_2-\overset{O}{\underset{\|}{C}}-.$$

R, $R_8$ and $R_9$ are independently selected from hydrogen, lower alkyl, benzyl, benzhydryl, and salt forming ion.

$R_1$ and $R_2$ are independently selected from hydrogen, halogen, lower alkyl, lower alkoxy, halo substituted lower alkyl, nitro, and $-SO_2NH_2$.

Z is $$-\overset{O}{\underset{\|}{C}}-\ \text{or}\ -\overset{O}{\underset{\|}{\underset{\|}{S}}}-.$$

$R_3$ is hydrogen, lower alkyl, halo substituted lower alkyl, phenyl, benzyl, phenethyl or cycloalkyl.

$R_4$ is hydrogen or $$R_5-\overset{O}{\underset{\|}{C}}-.$$

$R_5$ is lower alkyl,

[phenyl-$(CH_2)_n-$, thienyl-$(CH_2)_n-$, furyl-$(CH_2)_n-$ or pyridyl-$(CH_2)_n-$]

n is zero, one, two, three or four.
$R_6$ is hydrogen, lower alkyl, lower alkoxy, halogen, or hydroxy.
$R_7$ is lower alkyl or cycloalkyl.
$R_{10}$ is hydrogen, lower alkyl,

[phenyl-$(CH_2)_n-$], halo substituted lower alkyl, hydroxy substituted lower alkyl, $-(CH_2)_q-$cycloalkyl, $-(CH_2)_q-$N(lower alkyl)$_2$, $-(CH_2)_q-NH_2$, $-(CH_2)_q-$carboxy, $-(CH_2)_q-SH$, $-(CH_2)_q-$S-lower alkyl, $-(CH_2)_q-$phenyl-OH, $-(CH_2)_q-$indolyl, $-(CH_2)_q-$imidazolyl, $-(CH_2)_q-$guanidinyl, -continued

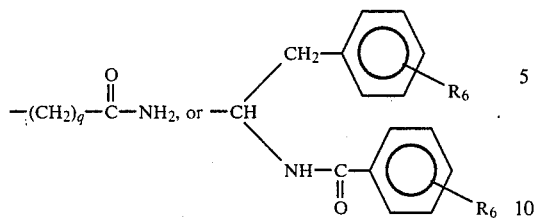

q is one, two, three or four.

$R_{11}$ is hydrogen, lower alkyl, halo substituted lower alkyl, hydroxy substituted lower alkyl, —$(CH_2)_q$-$NH_2$, —$(CH_2)_q$-N(lower alkyl)$_2$, —$(CH_2)_q$-guanidinyl,

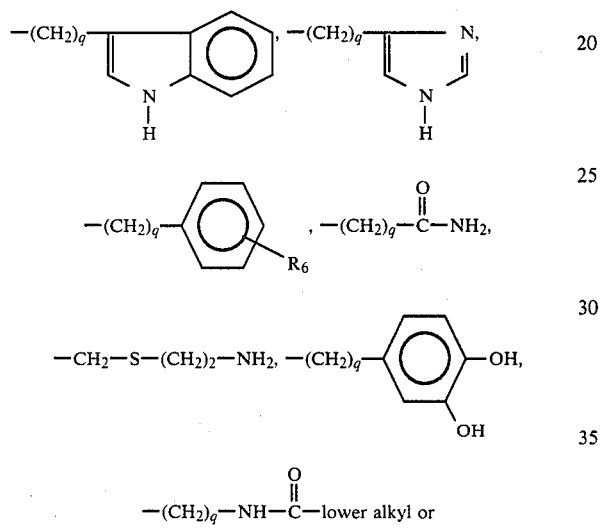

—$CH_2$—S—$(CH_2)_2$—$NH_2$,

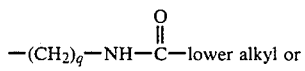

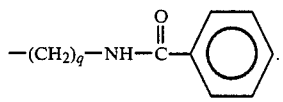

$R_{12}$ is alkyl of 1 to 10 carbons,

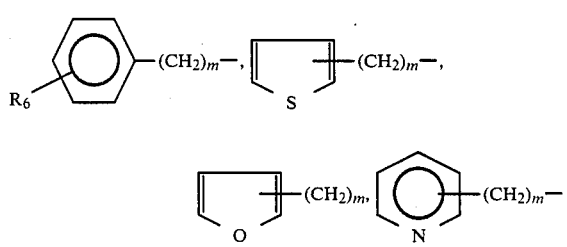

or cycloalkyl-$(CH_2)_m$—.

m is zero or an integer from 1 to 7.

$R_{13}$ is hydrogen, lower alkyl, benzyl, benzhydryl, salt forming ion or

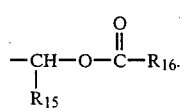

$R_{15}$ is hydrogen, lower alkyl, cycloalkyl or phenyl.

$R_{16}$ is hydrogen, lower alkyl, lower alkoxy, cycloalkyl, phenyl, benzyl, or phenethyl.

$R_{14}$ is hydrogen, lower alkyl, cycloalkyl-$(CH_2)_n$—,

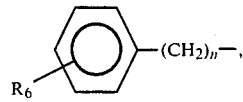

halo substituted lower alkyl, hydroxy substituted lower alkyl, —$(CH_2)_q$-N(lower alkyl)$_2$, or —$(CH_2)_q$-$NH_2$.

The symbols

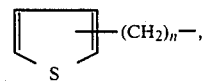

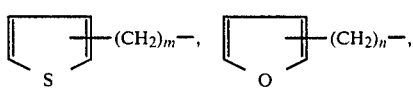

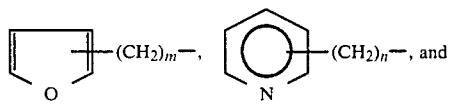

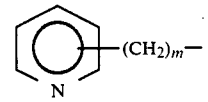

represent that the alkylene bridge is attached to an available carbon atom.

DETAILED DESCRIPTION OF THE INVENTION

This invention in its broadest aspects relates to the substituted 4-phenoxy and 4-phenylthio prolines of formula I above, to various intermediates for these compounds, to compositions containing such compounds and to the method of using such compounds as hypotensive agents.

The term lower alkyl as used in defining various symbols are straight or branched chain hydrocarbon radicals having up to seven carbons, for example, methyl, ethyl, propyl, isopropyl, butyl, t-butyl, pentyl, etc. The preferred lower alkyl groups are up to four carbons with methyl and ethyl being most preferred. Similarly, the term lower alkoxy refers to such lower alkyl groups attached to an oxygen.

The term halogen refers to chloro, bromo, and fluoro. The term halo substituted lower alkyl refers to such lower alkyl groups described above in which one or more hydrogens have been replaced by chloro, bromo, or fluoro groups such as trifluoromethyl, which is preferred, 2,2,2-trichloroethyl, chloromethyl, bromomethyl, etc. Similarly, the term hydroxy substituted lower alkyl refers to such lower alkyl groups in which one or more hydrogens have been replaced by hydroxy such as hydroxymethyl, 2-hydroxyethyl, etc.

The term cycloalkyl refers to saturated rings of 3 to 7 carbons with cyclopentyl and cyclohexyl being preferred.

The compounds of formula I wherein A is

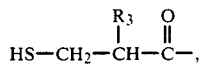

$A_1-A_2$ is —CH—NH—, and R is hydrogen are prepared by treating a compound of the formula

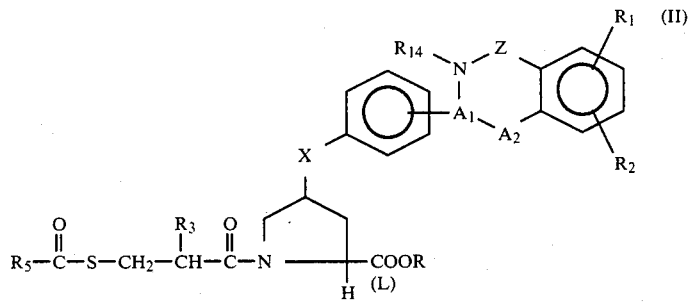

wherein R is a lower alkyl group such as methyl with base such as sodium hydroxide.

The compounds of formula II wherein $A_1-A_2$ is —CH—NH— are prepared by reacting a substituted phenoxy or phenylthio proline ester of the formula

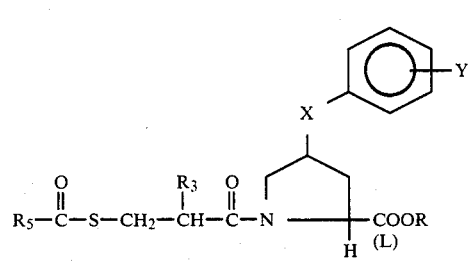

wherein Y is

—CH or —CH(lower alkoxy)$_2$ with a substituted benzenamine of the formula

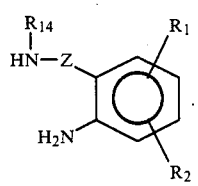

The intermediates of formula III are obtained by treating the 4-hydroxy substituted proline esters of the formula

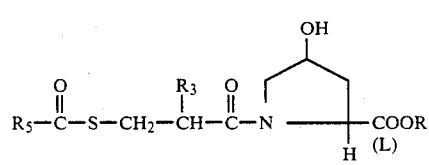

with the substituted phenol or thiophenol of the formula

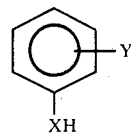

in the presence of triphenylphosphine and dialkylazodicarboxylate.

Similarly, the compounds of formula I wherein A is

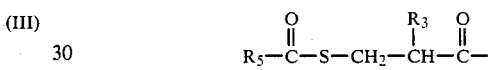

and R is hydrogen are prepared by treating a compound of formula II wherein R is an acid cleavable ester group such as benzhydryl with p-toluenesulfonic acid and anisole.

The benzhydryl ester compounds of formula II are prepared analogous to the above procedure except that the 4-hydroxy substituted proline acid of formula V (R is hydrogen) is treated with diphenyldiazomethane to yield the corresponding benzhydryl ester which is then reacted as described above.

The compounds of formula I wherein A is

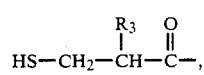

$A_1-A_2$ is —C≡N—, and R is hydrogen are prepared by treating a compound of the formula

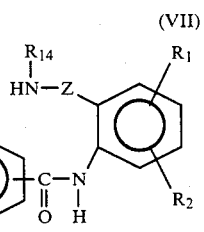

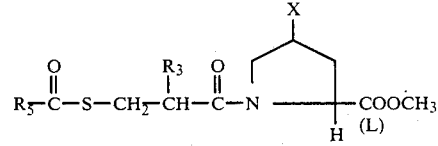

with a concentrated aqueous solution of ammonia, i.e., ammonium hydroxide, followed by treatment with sodium hydroxide to remove the methyl ester group.

The intermediates of formula VII are prepared by reacting a substituted phenoxy or phenylthio proline ester of the formula

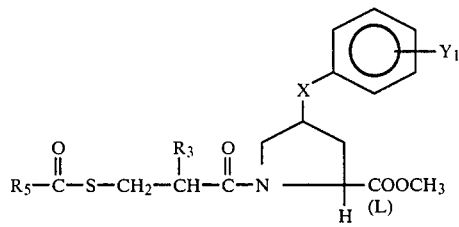

wherein $Y_1$ is

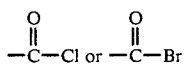

with a substituted benzeneamine of formula IV in a refluxing solvent such as dioxane. The compounds of formula VIII are prepared by treating the corresponding compound wherein $Y_1$ is COOH with an agent such as thionyl chloride or phosphorus tribromide in a solvent such as dichloromethane and with a catalyst such as dimethylformamide.

The compounds wherein $Y_1$ is COOH are prepared by reacting the ester compound of the formula

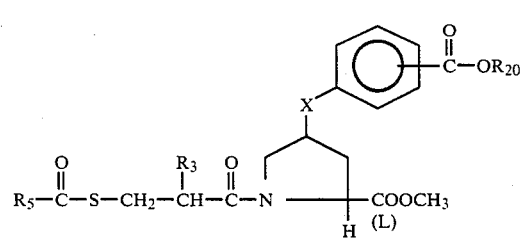

wherein $R_{20}$ is an acid cleavable group such as t-butyl or benzhydryl, with an acid such as trifluoroacetic acid or 97% formic acid.

The ester compounds of formula IX are prepared by treating the 4-hydroxy substituted proline ester of formula V wherein R is methyl with the substituted phenol or thiophenol of the formula

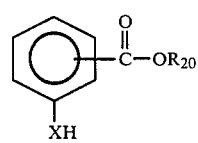

in the presence fo triphenylphosphine and dialkylazodicarboxylate.

The compounds of formula I wherein A is

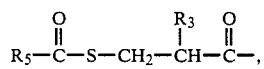

$A_1$—$A_2$ is —C=N—, and R is hydrogen are prepared by treating the corresponding compound wherein A is

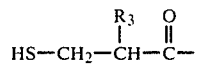

with an acid

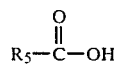

in the presence of a suitable activating agent such as dicyclohexylcarbodiimide or with an activated derivative such as

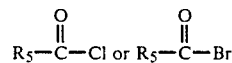

in the presence of a suitable acid acceptor such as pyridine or triethylamine.

The compounds of formula I wherein A is

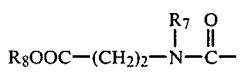

and $A_1$—$A_2$ is —CH—NH— are prepared by reacting a 4-hydroxy proline benzyl ester with an alkylaminopropanoate of the formula

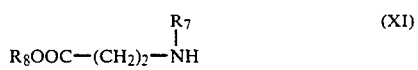

wherein $R_8$ is lower alkyl in the presence of phosgene and N-methylmorpholine to yield the substituted 4-hydroxy proline benzyl ester of the formula

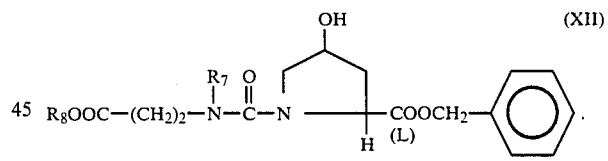

Treatment of the product of formula XII with the substituted phenol or thiophenol of formula VI in the presence of triphenylphosphine and dialkylazodicarboxylate yields the dimethoxymethyl intermediate of the formula

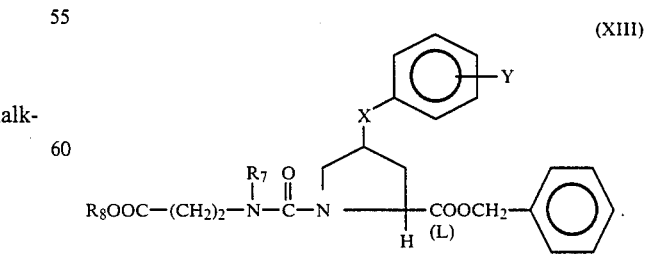

The intermediate of formula XIII is then reacted with the substituted benzenamine of formula IV to yield the proline benzyl ester

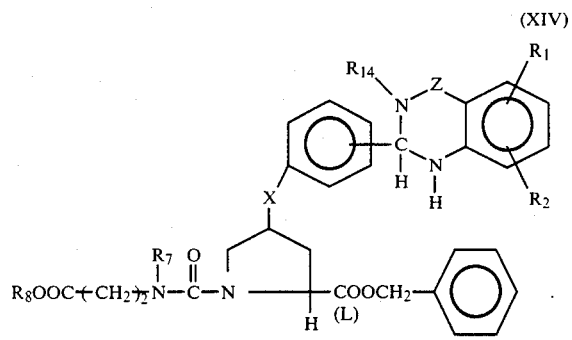

Hydrogenation of benzyl ester XIV with palladium/carbon removes the benzyl ester group and yields the products of formula I wherein $R_8$ is alkyl and R is hydrogen. Further treatment with aqueous sodium hydroxide yields the diacid product of formula I, i.e., both $R_8$ and R are hydrogen.

The compounds of formula I wherein A is

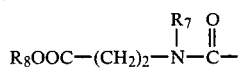

and $A_1$—$A_2$ is —C≡N— are prepared by reacting the 4-hydroxyproline benzyl ester of formula XII with the susbtituted phenol or thiophenol of formula X in the presence of triphenylphosphine and dialkylazodicarboxylate to give the compound of the formula

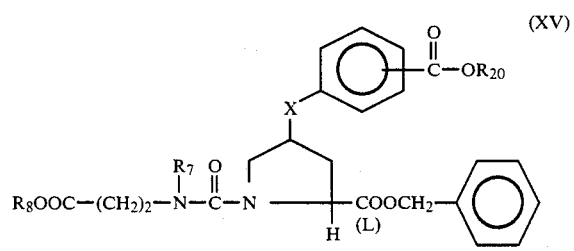

wherein $R_8$ is lower alkyl and $R_{20}$ is an acid cleavable group such as t-butyl or benzhydryl.

Treatment of the compound of formula XV with trifluoroacetic acid or 97% formic acid gives the compound of the formula

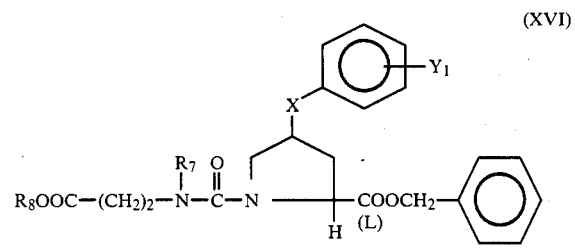

wherein $Y_1$ is —COOH. Treatment of the compound of formula XVI with an agent such as thionyl chloride or phosphorus tribromide as described above yield the compound wherein $Y_1$ is

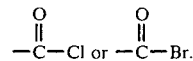

This intermediate is then reacted with the substituted benzeneamine of formula IV to give the compound of the formula

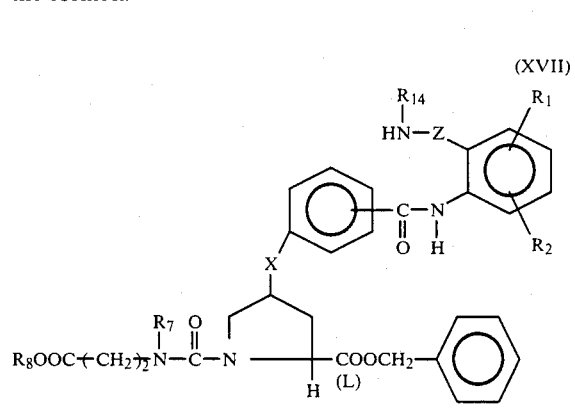

The compound of formula XVII is cyclized by treatment with a concentrated aqueous solution of ammonia to give the compound of the formula

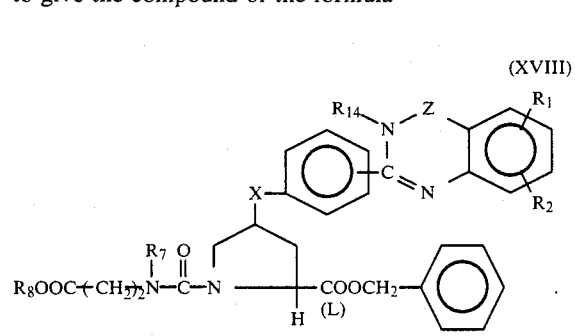

Hydrogenation of benzyl ester XVIII with palladium/carbon removes the benzyl ester group and yields the products of formula I wherein $R_8$ is alkyl and R is hydrogen. Further treatment with aqueous sodium hydroxide yields the diacid product of formula I, i.e., both $R_8$ and R are hydrogen.

The compounds of formula I wherein A is

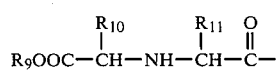

can be prepared by reacting an intermediate of the formula

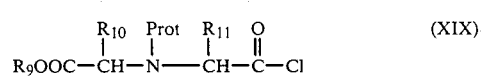

wherein Prot is a protecting group such as t-butoxycarbonyl with a functionalized proline ester of the formula

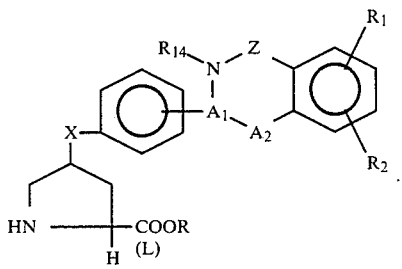

in aqueous sodium bicarbonate to give the compound of the formula

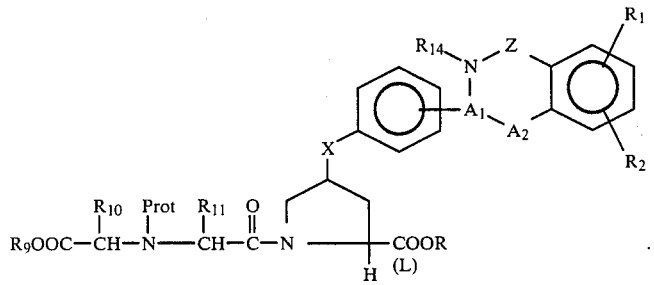

Removal of the Prot group such as by treatment with trifluoroacetic acid gives the desired products of formula I.

In these procedures when $R_9$ and $R$ are carboxy ester protecting group such as lower alkyl, benzyl or the like, they can be converted by known methods such as hydrolysis or hydrogenation to the products wherein $R$ and/or $R_9$ are hydrogen. Reductive cleavage of the diester product wherein $R$ is benzyl and $R_9$ is lower alkyl yields the monoester product wherein $R$ is hydrogen and $R_9$ is lower alkyl. Similarly, reductive cleavage of the diester product wherein $R$ is lower alkyl and $R_9$ is benzyl yields the monoester product wherein $R$ is lower alkyl and $R_9$ is hydrogen.

The compounds of formula I wherein A is

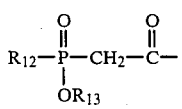

can be prepared by reacting a phosphinylacetic acid of the formula

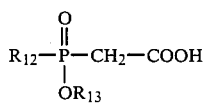

wherein $R_{13}$ is lower alkyl, benzyl or benzhydryl, with the functionalized proline ester of formula XX. The reaction can be accomplished using known amide bond forming procedures. For example, the reaction can be run in the presence of a coupling agent such as 1,1'-carbonyldiimidazole or the acid of formula XXII can be activated by formation of its mixed anhydride, symmetrical anhydride, acid halide, acid ester, etc.

The products of formula I wherein either or both of $R_{13}$ and $R$ are lower alkyl, benzyl, or benzhydryl can be hydrogenated, for example, by treating with hydrogen in the presence of a palladium on carbon catalyst or chemically treated such as with sodium hydroxide in aqueous dioxane or with trimethylsilylbromide in dichloromethane to yield the products of formula I wherein $R_{13}$ and $R$ are hydrogen.

The ester products of formula I wherein $R_{13}$ is

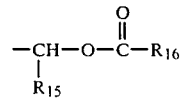

can be obtained by treating the product of formula I wherein $R_{13}$ is hydrogen or an alkali metal salt and $R$ is benzyl or benzhydryl with the compound of the formula

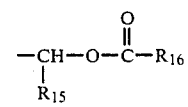

wherein L is a leaving group such as chlorine, bromine, tolylsulfonyloxy, etc., in the presence of base. Removal of the R ester group such as by hydrogenation yields the products of formula I wherein $R_{13}$ is

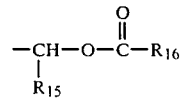

and R is hydrogen.

Of course, the products of formula I wherein A is

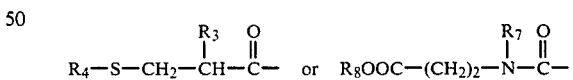

can also be prepared by coupling the appropriate sidechain with the functionalized proline ester of formula XX.

The starting materials of formula V are disclosed by Ondetti et al. in U.S. Pat. Nos. 4,105,776 and 4,316,906. The alkylaminopropanoates of formula XI are described in the Tanabe patent applications noted above. The starting materials of formula XIX are described by Patchett et al. in European Patent Application No. 12,401 and U.S. Pat. No. 4,374,829. The phosphinylacetic acid starting materials of formula XXII are described by Petrillo in U.S. Pat. Nos. 4,168,267 and 4,337,201.

The substituted benzenamines of formula IV are described in the literature as note, for example, Cohen et al., JACS, Vol. 82, p. 273(1960), Shetty et al., J. Med. Chem. Vol. 13, p. 886 (1970), and Close et al., JACS, Vol. 82, p. 1132.

The functionalized proline ester of formula XX wherein $A_1$—$A_2$ is —CH—NH— can be prepared by reacting an N-protected proline compound of the formula

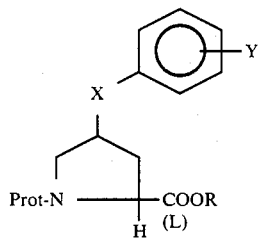

(XXIV)

wherein Prot is a protecting group such as t-butoxycarbonyl and Y is

or —CH(lower alkoxy)$_2$ with the substituted benzeneamine of formula IV in the presence of an acid such as toluenesulfonic acid and in a solvent such as acetonitrile.

The compound of formula XXIV can be prepared by reacting the 4-hydroxy-N-protected proline ester with the substituted phenol or thiophenol of formula VI in the presence of triphenylphosphine and dialkylazodicarboxylate.

The functionalized proline ester of formula XX wherein $A_1$—$A_2$ is —C≡N— can be prepared by reacting an N-protected proline compound of the formula

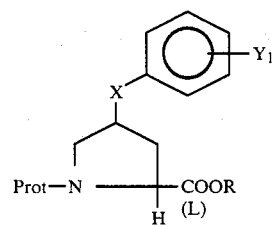

(XXV)

wherein Prot is a protecting group such as t-butoxycarbonyl and $Y_1$ is

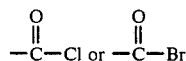

with the substituted benzeneamine of formula IV in a refluxing solvent such as dioxane.

The compounds of formula XXV are prepared from the corresponding compounds wherein $Y_1$ is —COOH by reacting with a reagent such as oxalyl chloride or phosphorus tribromide in the presence of the catalyst dimethylformamide in a solvent such as dichloromethane.

The corresponding carboxylic acid compounds of formula XXV can be prepared by treating the aldehyde, i.e., $Y_1$ is

with an oxidizing agent such as chromium trioxide in the presence of a mixture of pyridine and dichloromethane.

In the above reactions if any or all of $R_{10}$, $R_{11}$ and $R_{14}$ are amino or hydroxy substituted lower alkyl,

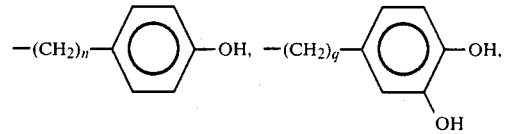

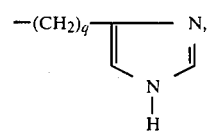

—$(CH_2)_q$-SH, or —$(CH_2)_q$-guanidinyl then the hydroxyl, amino, imidazolyl, mercaptan or guanidinyl function should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known means following completion of the reaction.

Preferred compounds of this invention are those of formula I wherein

X is oxygen.

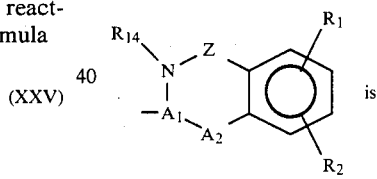 is

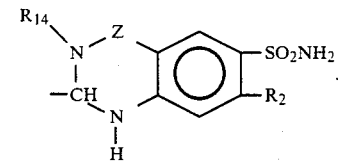

R is hydrogen, lower alkyl of 1 to 4 carbons, or an alkali metal salt ion.

$R_{14}$ is hydrogen or lower alkyl of 1 to 4 carbons, especially hydrogen or methyl.

$R_2$ is halogen, lower alkyl of 1 to 4 carbons, or halo substituted lower alkyl of 1 to 4 carbons, especially chloro or trifluoromethyl.

$R_4$ is hydrogen or

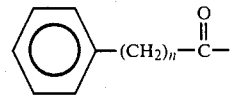

wherein n is zero, one, or two, especially hydrogen or

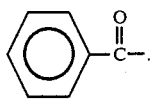

$R_3$ is lower alkyl of 1 to 4 carbons, especially methyl.
$R_8$ is hydrogen, lower alkyl of 1 to 4 carbons, or an alkali metal salt ion, especially hydrogen, ethyl, or an alkali metal salt ion.
$R_7$ is lower alkyl of 1 to 4 carbons, especially ethyl.
$R_9$ is hydrogen, lower alkyl of 1 to 4 carbons, or an alkali metal salt ion, especially hydrogen, ethyl, or an alkali metal salt ion.
$R_{10}$ is

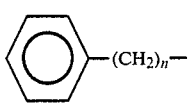

wherein n is zero, one, two, three, or four, especially

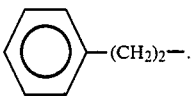

$R_{11}$ is lower alkyl of 1 to 4 carbons, $-CH_2-S-(CH_2)_2-NH_2$, or $-(CH_2)_4-NH_2$, especially methyl.
$R_{12}$ is alkyl of 1 to 10 carbons or

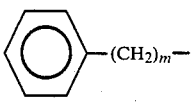

wherein m is zero or an integer from 1 to 7, especially

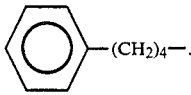

$R_{13}$ is hydrogen, alkali metal salt ion, or

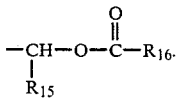

$R_{15}$ is hydrogen, straight or branched chain lower alkyl of 1 to 4 carbons, or cyclohexyl.
$R_{16}$ is straight or branched chain lower alkyl of 1 to 4 carbons.

The compounds of formula I give rise to cis-trans isomerism at the 4-position of the proline ring. The configuration of the final product depends upon the configuration of the 4-hydroxy proline starting material. When the hydroxy group is in the trans-configuration, the substituted phenol or phenylthiol intermediate is obtained in the cis-configuration and this configuration is maintained throughout the remainder of the reaction sequence. Similarly, if a cis-hydroxy starting material is employed the final product will be obtained in the trans configuration.

The compounds wherein A is

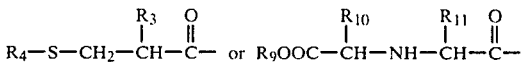

and $R_3$, $R_{10}$ and $R_{11}$ are other than hydrogen contain one or more additional asymmetric centers. These products of formula I can accordingly exist in stereoisomeric forms or as racemic mixtures thereof. The synthesis described above can utilize the racemate or one of the enantiomers as starting materials. When the racemic starting material is used in the synthetic procedure, the stereoisomers obtained in the final product can be separated by chromatographic techniques such as Pirkel or flash chromatography or fractional crystallization methods.

Preferably, if there is an asymmetric center in the sidechain it is in the S-configuration.

The compounds of this invention wherein at least one of R, $R_8$, $R_9$ and $R_{13}$ is hydrogen, form salts with various inorganic and organic bases which are also within the scope of the invention. Such salts include ammonium salts, alkali metal salts like lithium, sodium and potassium salts (which are preferred), alkaline earth metal salts like calcium and magnesium salts, salts with organic bases, e.g., dicyclohexylamine salt, benzathine, N-methyl-D-glucamine, salts with amino acids like arginine, lysine and the like. The nontoxic, physiologically acceptable salts are preferred, although other salts are also useful, e.g., in isolating or purifying the product. The salts are formed using conventional techniques.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. The compounds of formula I also possess diuretic activity. Thus, by the administration of a composition containing one or a combination of the compounds of the invention, hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade. AG-50W-X8 refers to a crosslinked polystyrene divinylbenzene sulfonic acid cation exchange resin. HP-20 refers to a porous crosslinked polystyrene-divinyl benzene polymer resin.

EXAMPLE 1

[1(S),4S]-4-[3-[6-(Aminosulfonyl)-7-chloro-1,2,3,4-tetrahydro-4-oxo-2-quinazolinyl]phenoxy]-1(3-mercapto-2-methyl-1-oxopropyl)-L-proline (a)

[1(S),4R]-1-[3-(Benzoylthio)-2-methyl-1oxopropyl]-4-hydroxy-L-proline, methyl ester (D)-3-(Benzoylthio)-2-methylpropanoic acid (56.05 g., 0.25 mole) is suspended in 62.5 ml. of toluene. The temperature falls to 15° and then 0.386 ml. of dimethylformamide is added. Then 32.7 g. (0.25 mole 10% excess) of thionyl chloride is added all at once with stirring. The temperature of the reaction mixture falls to 12° and the container used to measure the thionyl chloride is rinsed with 21.2 ml. of toluene which is then added to the reaction mixture. The temperature is raised gradually to 35° and maintained there for one hour. The reaction mixture is allowed to stir at room temperature overnight. The solvent and excess thionyl chloride are removed and the residue is treated twice with 100 ml. of toluene after which the toluene is removed to yield 63.4 g. of (D)-3-(benzoylthio)-2-methylpropanoic acid chloride.

L-4-Hydroxyproline (32.7 g., 0.25 mole) is dissolved in 250 ml. of water at pH 5.8. About 60 ml. of 10% sodium carbonate is added to bring the pH to 9.3. The solution is warmed to 30° and a toluene solution (75 ml.) containing 63 g. of (D)-3-(benzoylthio)-2-methylpropanoic acid chloride is added simultaneously with 10% aqueous sodium carbonate over one hour at 30° maintaining the pH at 9.0. The solution is stirred at pH 9.0 for 1.5 hours and the toluene layer is separated off. The aqueous layer is made strongly acid with concentrated HCl and the crystalline solid is filtered, washed with water, and air-dried to yield 71.4 g. of [1(S),4R]-1-[3-(benzoylthio)-2-methyl-1oxopropyl]-4-hydroxy-L-proline; m.p. 195–196°. Recrystallization from alcohol gives a m.p. of 196–197°; $[\alpha]_D^{25}$ −139° (c=1, methanol).

Anal. Calc'd. for $C_{16}H_{19}NO_5S$:
N, 4.15; C, 56.95; H, 5.67; S, 9.50.
Found: N, 3.96; C, 56.56; H, 5.77; S, 9.50.

A solution of 33.7 g. (0.1 mole) of [1(S),4R]-1-[3-(benzoylthio)-2-methyl-1oxopropyl]-4-hydroxy-L-proline and 500 mg. of p-toluenesulfonic acid in 1 l. of methanol is gently refluxed for about 18 hours. The methanol is removed to yield 37 g. of a viscous residue which is dissolved in 1400 ml. of ether. The ether solution is washed twice with 250 ml. of water, twice with 250 ml. of 5% sodium bicarbonate, and once with 250 ml. of brine and dried over $MgSO_4$. The ether is removed to yield 27.3 g. of crystalline product (after trituration with petroleum ether); m.p. 64°–65°. Recrystallization from ether yields [1(S),4R]-1-[3-(benzoylthio)-2-methyl-yl-1-oxopropyl]-4-hydroxy-L-proline, methyl ester; m.p. 65.5°–67°; $[\alpha]_D^{25}$ −158° (c =1, methanol).

Anal. Calc'd. for $C_{17}H_{21}NO_5S$:
N, 3.99; C, 58.10; H, 6.02; S, 9.12.
Found: N, 3,96; C, 57.96; H, 6.09; S, 9.11.

(b) 3-(Dimethoxymethyl)phenol

To a mixture of 12.2 g. (0.1 mole) of 3-hydroxybenzaldehyde and 11.0 ml. of trimethyl orthoformate in 8 ml. of methanol there is added 1 drop of concentrated hydrochloric acid. The reaction mixture becomes warm. The reaction mixture is heated to 55° for 1.5 hours, then cooled and the solvent is removed in vacuo. The dark colored residue is dissolved in ethyl ether, filtered, and evaporated in vacuo to give 6.5 g. of greenish liquid 3-(dimethoxymethyl)phenol. Tlc (ethyl ether) $R_f=0.8$ (single spot).

(c)

[1(S),4S]-1-[3-(Benzoylthio)-2-methyl-1-oxopropyl]-4-[3-(dimethoxymethyl)phenoxy]-L-proline, methyl ester To a solution of 4.2 g. (0.012 mole) of 1(S),4R]-1-[3-(benzoylthio)-2-methyl-1-oxopropyl]-4-hydroxy-L-proline, methyl ester, 3 g. (0.0178 mole) of 3-(dimethoxymethyl) phenol and 4.6 g. (0.0175 mole) of triphenylphosphine in 15 ml. of dry tetrahydrofuran there is added 3.1 g. of diethylazodicarboxylate in 5 ml. of dry tetrahydrofuran (reaction mixture becomes warm) and the mixture is stirred overnight at room temperature under argon. The solvent is removed in vacuo and the resulting oil is dissolved in 20 ml. of 1:1 petroleum ether/ethyl ether. The mixture is seeded with dicarbethoxyhydrazine and allowed to stand at room temperature for 1 hour. The resulting solid is filtered off and washed with ethyl ether. The filtrate is preabsorbed on Baker silica gel and flash chromatographed. Elution with 4 l. of petroleum ether/ethyl ether (1:1) followed by 1 l. of petroleum ether/ethyl ether (1:9) yields 0.9 g. of pure [1(S),4S]-1-[3-(benzoylthio)2-methyl-1-oxopropyl]-4-[3-(dimethoxymethyl)phenoxy]-L-proline, methyl ester as a colorless viscous oil. Tlc (ethyl ether) $R_f=0.4$.

(d) 2-Amino-4-chloro-5-sulfamylbenzamide

A solution of 14 g. of 4-chloro-5sulfamyl-N-acetylanthranilic acid and 84 ml. of 3N sodium hydroxide is refluxed for 3 hours, filtered, and the filtrate is adjusted to pH 6. The flocculant material is filtered off and the filtrate is adjusted to pH 3. The resulting solid is filtered off and dried to yield 10.8 g. of 4-chloro-5-sulfamylanthranilic acid; m.p. 276°–277° (dec.).

A solution of 10 g. of 4-chloro-5sulfamylanthranilic acid, 100 ml. of methanol and 5 ml. of concentrated sulfuric acid is refluxed for 24 hours, cooled and poured into 700 ml. of concentrated ammonia and stirred at room temperature for 7 days during which time the solution becomes clear. The solution is partially evaporated in vacuo until a white solid formed. The solid is filtered off to yield 5.3 g. of 2-amino-4-chloro-5-sulfamylbenzamide; m.p. 278°–280°.

(e)

[1(S),4S]-4-[3-[6-(Aminosulfonyl)-7-chloro-1,2,3,4-tetrahydro-4-oxo-2-quinazolinyl]phenoxy]-1-[3-(benzoylthio)-2-methyl-1-oxopropyl]-L-proline, methyl ester A mixture of 0.5 g. (0.001 mole) of [1(S),4S]-1-[3-(benzoylthio)-2-methyl-1-oxopropyl]-4-[3-(dimethoxymethyl)phenoxy]-L-proline, methyl ester and 0.25 g.

of 2-amino-4-chloro-5-sulfamylbenzamide in 10 ml. of acetonitrile is treated with 0.001 g. of p-toluenesulfonic acid (transient yellow color) and the mixture is refluxed for 1 hour. The solvent is removed in vacuo and the residue is triturated with ethyl ether to yield a solid which is dissolved in dimethyl sulfoxide. The dimethyl sulfoxide solution is diluted with water and the resulting solid is filtered off and dried overnight at 80° to yield 0.5 g. of [1(S),4S]-4-[3-[6-(aminosulfonyl)-7-chloro-1,2,3,4-tetrahydro-4-oxo-2-quinazolinyl]phenoxy]-1-[3-(benzoylthio)-2-methyl-1-oxopropyl]-L-proline,methyl ester; m.p. 125° (dec.). Tlc (ethyl acetate) $R_f$=0.3 visualized with vanillin; (dichloromethane/methanol/acetic acid; 90:5:5) $R_f$=0.8 visualized with PMA.

Anal. Calc'd. for $C_{31}H_{31}ClN_4O_8S_2$ 19 $0.5H_2O$:
C, 53.56; H, 4.49; N, 8.06; Cl, 5.10; S, 9.22.
Found: C, 53.64; H, 4.50; N, 7.99; Cl, 4.75; S, 9.18.

(f)

[1(S),4S]-4-[3-[6-(Aminosulfonyl)-7-chloro-1,2,3,4-tetrahydro-4-oxo-2-quinazolinyl]phenoxy]-1-[3-mercapto-2-methyl-1-oxopropyl)-L-proline A mixture of 1 g. of [1(S),4S]-4-[3-[6(aminosulfonyl)-7-chloro-1,2,3,4-tetrahydro-4oxo-2-quinazolinyl]phenoxy]-1-[3-(benzoylthio)-2methyl-1-oxopropyl]-L-proline, methyl ester, 20 ml. of methanol, and 80 ml. of 0.2 N sodium hydroxide is stirred at room temperature for 8 hours. After this time, Tlc indicated the complete absence of starting material and mono ester. The reaction mixture is then acidified with 5% potassium bisulfate. The resulting solid is collected by filtration, washed with distilled water, and then dried in vacuo to yield 700 mg. of crude product. The crude reaction product is dissolved in 15 ml. of methanol and chromatographed on 50 g. of Sephadex (LH - 20 column), by gravity, eluting with methanol to yield 630 mg. of [1(S),4S]-4-[3-[6-(aminosulfonyl)-7-chloro-1,2,3,4-tetrahydro-4-oxo-2-quinazolinyl]phenoxy]- 1-(3-mercapto-2-methyl-1-oxopropyl)-L-proline; m.p. 180°-190°. Tlc (silica gel;dichloromethane (8)/methanol (1)/acetic acid (1)) $R_f$=0.5.

Anal. Calc'd. for $C_{23}H_{25}ClN_4O_7S_2 \cdot 0.5\ H_2O$:
C, 47. 79; H, 4.53; N, 9.69; Cl, 6.13; S, 11.07; SH, 5.77.
Found: C, 47.80; H, 4.66; N, 9.47; Cl, 6.08; S, 10.91; SH, 5.77.

EXAMPLE 2

[1(S),4S]-4-[2-[6-(Aminosulfonyl)-7-chloro-1,2,3,4-tetrahydro-4-oxo-2-quinazolinyl]phenoxy]-1-(3-mercapto-2-methyl-1-oxopropyl)-L-proline (a) 2-(Dimethoxymethyl)phenol To a mixture of 24.4 g. of salicylaldehyde, 25 g. of trimethyl orthoformate, and 50 g. of methanol there is added 0.1 ml. of concentrated hydrochloric acid. The temperature rises at once and the solution is kept at 55° for 1 hour. Then the reaction mixture is concentrated in vacuo and the remaining oil is fractionated at 85°-90° / 0.05 mm. to yield 15 g. of 2-(dimethoxymethyl)phenol as a viscous, colorless oil.

(b)

[1(S),4S]-1-[3-(Benzoylthio)-2-methyl-1-oxo-propyl]-4-[2-(dimethoxymethyl)phenoxy]-L-proline, methyl ester To a mixture of 4.2 g. of [1(S),4R]-1-[3-(benzoylthio)-2-methyl-1-oxopropyl]-4-hydroxy-L-proline, methyl ester, 3 g. of 2-(dimethoxymethyl)-phenol, 4.6 g. of triphenylphosphine dissolved in 15 ml. of tetrahydrofuran there is added 3.1 g. of diethylazodicarboxylate dissolved in 5 ml. of tetrahydrofuran (nitrogen atmosphere). The mixture becomes warm. The solution is stirred overnight. Addition of ether/petroleum ether yields 1.1 g. of dicarbethoxyhydrazine which is filtered off. Addition of more petroleum ether to the filtrate furnishes oily triphenylphosphine oxide which on trituration with ether turns solid; 2.5 g. The filtrate is absorbed on Baker silica and flash chromatographed. Elution with 85% ether - 10% petroleum ether elutes the pure product in six fractions, 250 ml. each, yielding 2.99 g. of [1(S),4S]-1-[3-(benzoylthio)-2methyl-1-oxopropyl]-4-[2-(dimethoxymethyl)phenoxy]-L-proline, methyl ester. A small sample is characterized and analyzed as its 2,4-dinitrophenyl hydrazine derivative.

Anal. Calc'd. for $C_{30}H_{29}N_5O_9S$:
C, 56.68; H, 4.60; N, 11.02; S, 5.04.
Found: C, 56.43; H, 4.58; N, 10.99; S, 5.04.

(c)

[1(S),4S]-4-[2-[6-(Aminosulfonyl)-7-chloro-1,2,3,4-tetrahydro-4-oxo-2-quinazolinyl]phenoxy]-1-[3-(benzoylthio)-2-methyl-1-oxopropyl]-L-proline, methyl ester A mixture of 0.25 g. of 2-amino-4-chloro-5-sulfamylbenzamide, 0.5 g. of [1(S),4S]-1-[3-(benzoylthio)-2-methyl-1-oxopropyl]-4-[2-(dimethoxy-methyl)phenoxy]-L-proline, methyl ester, and 0.1 g. of p-toluenesulfonic acid in 20 ml. of acetonitrile is refluxed overnight. About 10 ml. of solvent is removed in vacuo and the resulting solution is treated with enough ether to give complete precipitation of the product. The solid is filtered off and reprecipitated from dimethylformamide-water to yield 0.5 g. of [1(S),4S]-4-[2-[6-(aminosulfonyl)-7-chloro-1,2,3,4-tetrahydro-4-oxo-2-quinazolinyl]phenoxy]-1-[3-(benzoylthio)-2-methyl-1-oxopropyl]-L-proline, methyl ester. Tlc (dichloromethane/methanol/acetic acid; 90:5:5) $R_f$=0.61 visualized with PMA.

Anal. Calc'd. for $C_{31}H_{31}ClN_4O_8S_2$:
C, 53.47; H, 4.49; N, 8.05; Cl, 5.09; S, 9.21.
Found: C, 53.25; H, 4.49; N, 8.07; Cl, 4.87; S, 8.97.

(d)

[1(S),4S]-4-[2-[6-(Aminosulfonyl)-7-chloro-1,2,3,4-tetrahydro-4-oxo-2-quinazolinyl]phenoxy]-1-(3-mercapto-2-methyl-1-oxopropyl)-L-proline A mixture of 0.52 g. of [1(S),4S]-4-[2-[6-(aminosulfonyl)-7-chloro-1,2,3,4-tetrahydro-4-oxo-2-quinazolinyl]phenoxy]-1-[3-(benzoylthio)-2-methyl-1-oxopropyl]-L-proline, methyl ester, 10 ml. of methanol, and 2 ml. of 2N sodium hydroxide is stirred at room temperature for 1 hour (nitrogen atmosphere). At this time, no starting material is detectable by Tlc but a certain quantity of mono ester is still present. Thus, an additional 2 ml. of 2N sodium hydroxide is added and after two additional hours of stirring the reaction mixture is acidified with 10% potassium bisulfate. The resulting white precipitate is filtered off, washed with water and dried yielding 0.37 g. of [1(S),4S]-4-[2-[6-(aminosulfonyl)-7-chloro-1,2,3,4-tetrahydro-4-oxo-2-quinazolinyl]phenoxy]-1-(3-mercapto-2-methyl-1-oxopropyl)-L-proline; m.p. 190°-195° (softening at 150° ). Tlc (dichloromethane/methanol/acetic acid; 90:5:5) $R_f$=0.21 visualized with PMA.

Anal. Calc'd. for $C_{23}H_{25}ClN_4O_7S_2 \cdot 0.8\ H_2O$:
C, 47.34; H, 4,59; N, 9.60; Cl, 6.08; S,10.99.
Found: C, 47.34; H, 4.45; N, 9.95; Cl, 5.98; S,10.73.

EXAMPLE 3

[1(S),4S]-4-[4-[6-(Aminosulfonyl)-7-chloro-1,2,3,4-tetrahydro-4-oxo-2-quinazolinyl]phenoxy]-1-(3-mercapto-2-methyl-1-oxopropyl)-L-proline (a) 4-(Dimethoxymethyl)phenol A solution of 5 g. (0.04 mole) of 4-hydroxybenzaldehyde in 25 ml. of methanol is treated with a drop of concentrated hydrochloric acid and stored at 25° overnight. Then several scoops each of sodium bicarbonate and sodium sulfate are added and swirled for 10 minutes. The slurry is filtered, evaporated in vacuo, and the residue taken up in ether, filtered and evaporated. Evaporation with ethyl acetate and finally hexane gives 4.5 g. of solid 4-(dimethoxymethyl) phenol.

(b)
[1(S),4S]-1-[3-(Benzoylthio)-2-methyl-1-oxopropyl]-4-[4-(dimethoxymethyl)phenoxy]-L-proline, methyl ester A solution of 6.18 g. (0.018 mole) [1(S),4R]-1-[3-(benzoylthio)-2-methyl-1-oxopropyl]-4-hydroxy-L-proline, methyl ester, 4.61 g. (0.018 mole) of triphenylphosphine and 2.96 g. of 4-(dimethoxymethyl)phenol in 75 ml. of dry tetrahydrofuran at 0° under argon is treated with a solution of 3.07 g. (0.018 mole) of diethylazodicarboxylate in 5 ml. of tetrahydrofuran, and the mixture is allowed to come to 25° overnight. Tlc on silica (ethyl ether elution)shows considerable starting material as well as product. Therefore, another 2.96 g. (0.018 mole) of 4-(dimethoxymethyl)phenol is added (mixture turns green), followed by 4.6 g. (0.018 mole) of triphenylphosphine (still green) and 3.07 g. (0.018 mole) of diethylazodicarboxylate (back to yellow). After 9 hours at 25° virtually all of the starting material has disappeared (by Tlc). Two chromatographic purifications on 60–200 mesh silica in ether gives 4 g. of material which have a single spot by Tlc with ether, but two closely running spots in hexane/acetone (2:1). These are completely separated on the Waters 500 preparative LC on two silica columns in hexane/acetone (4:1); the mixture being injected in benzene. The less polar material (1.7 g.) is determined by proton and carbon NMR to be [1(S),4S]-1-[3-(benzoylthio)-2-methyl- 1-oxopropyl]-4-[4-(dimethoxymethyl)phenoxy]-L-proline, methyl ester.

(c)
[1(S),4S]-4-[4-[6-(Aminosulfonyl)-7-chloro-1,2,3,4-tetrahydro-4-oxo-2-quinazolinyl]phenoxy]-1-[3-(benzoylthio)-2-methyl-1-oxo-propyl]-L-proline, methyl ester A slurry of 1.2 g. (2.4 mmole) of [1(S),4S]-1-[3-(benzoylthio)-2-methyl-1-oxopropyl]-4-[4-(dimethoxymethyl)phenoxy]-L-proline, methyl ester and 0.6 g. (2.4 mmole) of 2-amino-4-chloro-5-sulfamylbenzamide in 50 ml. of dry acetonitrile is treated with 25 mg. of p-toluenesulfonic acid and refluxed for 3 hours. Tlc (silica, ethyl acetate) shows one major spot ($R_f=0.2$). The mixture is evaporated and triturated with isopropyl ether to give [1(S),4S]-4-[4-[6-(aminosulfonyl)-7-chloro-1,2,3,4-tetrahydro-4-oxo-2-quinazolinyl]phenoxy]1-[3-(benzoylthio)-2-methyl-1-oxopropyl]-L-proline, methyl ester as a crude solid. (cl (d) [1(S),4S]-4-[4-[6-(Aminosulfonyl)-7-chloro-1,2,3,4-tetrahydro-4-oxo-2-quinazolinyl]phenoxy]1-(3-mercapto-2-methyl-1-oxopropyl)-L-proline The entire sample of the crude product from part (c) is dissolved in 100 ml. of argon purged 0.2 N sodium hydroxide and kept under argon for 1 hour, pH = 14. Acidification (10% potassium bisulfate) and extraction with ethyl acetate, drying ($Na_2SO_4$), and evaporation gives 1.1 g. of white solid which shows 6 spots on Tlc [silica:dichloromethane(8)/methanol(1)/acetic acid(1)]-two of which ($R_f=0.37$, 0.7) fluoresce bright blue under short wave UV irradiation. Chromatography on 200 g. of Sephadex (LH 20) in methanol gives the two fluoresing materials (as a mixture) as the first material off the column. Evaporation gives 0.8 g. of a foam. This material is dissolved in methanol-ethyl acetate and shaken with aqueous bicarbonate. The less polar material stayed in the organic layer. Acidification of the aqueous layer (10% potassium bisulfate) and extraction with ethyl acetatemethanol affords after drying ($Na_2SO_4$) and evaporation, the pure more polar product. This compound is dissolved in methanol, the solution filtered (millipore) and evaporated, and the resulting glass triturated with ether to give 0.5 g. of white solid [1(S),4S]-4-[4-[6-(aminosulfonyl)-7-chloro-1,2,3,4-tetrahydro-4-oxo-2-quinazolinyl]phenoxy]-1-(3-mercapto-2-methyl-1-oxopropyl-L-proline; m.p. 190°–210°.

Anal. Calc'd. for $C_{23}H_{25}ClN_4O_7S_2$:
C, 48.54; H, 4.43; N, 9.85; S, 11.27;
Cl, 6.23; SH, 5.81.
Found: C, 48.64; H, 4.78; N, 9.49; S, 11.19;
Cl, 6.51; SH, 5.67.

EXAMPLE 4

[1(S),4S]-4-[4-[6-(Aminosulfonyl)-7-chloro-1,2,3,4-tetrahydro-4-oxo-2-quinazolinyl]phenoxy]-1-[3-(benzoylthio)-2-methyl-1-oxopropyl]-L-proline (a)
[1(S),4R]-1-[3-(Benzoylthio)-2-methyl-1-oxopropyl]-4-hydroxy-L-proline, diphenylmethyl ester An ether solution of diphenyldiazomethane is added to a slurry of [1(S),4R]-1-[3-(benzoylthio)-2-methyl-1-oxopropyl]-4-hydroxy-L-proline (5 g./100 ml. of dichloromethane). The reaction mixture is stirred at room temperature overnight. The reaction solution is then evaporated to residue. The residue is taken up in dichloromethane and washed with 1N sodium bicarbonate and brine. The solution is then dried ($Na_2SO_4$) and evaporated to a residue which is triturated with ether and recrystallized from ethyl acetate to give 6 g. of pure [1(S),4R]-1-[3-(benzoylthio)-2-methyl-1-oxopropyl]-4-hydroxy-L-proline, diphenylmethyl ester as a white crystalline solid.

(b)
[1(S),4S]-1-[3-(Benzoylthio)-2-methyl-1-oxopropyl]-4-[4-(dimethoxymethyl)phenoxy]-L-proline,diphenylmethyl ester To a stirred mixture of 5.04 g. (10 mmole) of [1(S),4R]-1-[3-(benzoylthio)-2-methyl-1-oxopropyl]-4-hydroxy-L-proline, diphenylmethyl ester, 2.52 g. (15 mmole) of 4-(dimethoxymethyl)phenol, and 3.93 g. (15 mmole) of triphenylphosphine in 15 ml. of dry tetrahydrofuran under argon at 0° is added dropwise a solution of diethylazodicarboxylate (2.61 g., 15 mmole) in 5 ml. of tetrahydrofuran. The reaction mixture is stirred at ambient temperature for approximately 64 hours and then concentrated to a residue. The residue is chromatographed on a gravity silica gel column (diethyl ether eluant) followed by Waters Prep. layer chromatography using hexane:acetone (4:1) to give [1(S),4S]-1-[3-(benzoylthio)-2-methyl-1-oxopropyl]-4-[4-(dimethoxymethyl)phenoxy]-L-proline, diphenylmethyl ester.

(c)

[1(S),4S]-4-[4-[6-(Aminosulfonyl)-7-chloro-1,2,3,4-tetrahydro-4-oxo-2-quinazolinyl]phenoxy]-1-[3-(benzoylthio)-2-methyl-1-oxopropyl]-L-proline 1 g. (1.5 mmole) of [1(S),4S]-1-[3-(benzoylthio)-2-methyl-1-oxopropyl]-4-[4-(dimethoxymethyl) phenoxy]-L-proline, diphenylmethyl ester, 0.5 g. (2 mmole) of 2-amino-4-chloro-5-sulfamylbenzamide, and anisole (2 ml.) are combined in approximately 20 ml. of acetonitrile. A catalytic amount (50 mg.) of p-toluenesulfonic acid is added and the reaction mixture is heated at reflux for 1 hour. After evaporation of the solvent, the residue is taken up in ethyl acetate and water. The aqueous layer is discarded. The product is extracted into a sodium bicarbonate solution, washed with ethyl acetate and reacidified using potassium bisulfate. Upon acidification the product is extracted into fresh ethyl acetate. After washing with water and brine and drying (MgSO$_4$), the solvent is evaporated to give a white solid. Purification is done on a Sephadex LH20 column (methanol). Trituration with ether gives [1(S),4S]-4-[4-[6-(aminosulfonyl)-7-chloro-1,2,3,4-tetrahydro-4-oxo-2-quinazolinyl]phenoxy]-1-[3-(benzoylthio)-2-methyl-1-oxopropyl]-L-proline as a white crystalline solid.

Anal. Calc'd. for $C_{30}H_{29}ClN_4O_8S_2 \cdot 0.25\ H_2O$:
C, 53.17; H, 4.39; N, 8.27; S, 9.46; Cl, 5.23.
Found: C, 53.15; H, 4.47; N, 8.08; S, 9.17; Cl, 5.17.

EXAMPLE 5

[1(S),4S]-4-[4-[7-(Aminosulfonyl)-6-chloro-3,4-dihydro-1,1-dioxo-2H-1,2,4-benzothiadiazin-3-yl]phenoxy]-1-(3-mercapto-2-methyl-1-oxopropyl)-L-proline (a)

[1(S),4S]-4-[4-[7-(Aminosulfonyl)-6-chloro-3,4-dihydro-1,1-dioxo-2H-1,2,4-benzothiadiazin-3-yl]phenoxy]-1-[3-(benzoylthio)-2-methyl-1-oxopropyl]-L-proline, methyl ester A slurry of 450 mg. (0.9 mmole) of [1(S),4S]-1-[3-(benzoylthio)-2-methyl-1-oxopropyl]-4-[4-(dimethoxymethyl)phenoxy]-L-proline, methyl ester and 280 mg. (1.0 mmole) of 4-amino-6-chloro-1,3-benzenedisulfonamide in 10 ml. of acetonitrile is treated with 20 mg. of p-toluenesulfonic and the resulting mixture was heated to reflux for 13 hours. The solvent is evaporated in vacuo and the residue taken up in ethyl acetate and passed through a 40 ml. silica (60-200 mesh) pad to remove some polar (Tlc on silica, hexane/acetone 2:1) impurities. Trituration of the residue from the evaporation of the ethyl acetate with dichloromethane removes the less polar impurities ($R_f$=0.8 - 0.9) leaving the desired product and unreacted L-proline starting material. This mixture is taken up in 40 ml. of acetonitrile, filtered, and then diluted with water to give a milky white mixture. This is filtered on Celite and the pad washed with water. The Celite pad is then extracted with acetonitrile and the extracts evaporated to a slurry. This is taken up in ethyl acetate, dried (Na$_2$SO$_4$), and evaporated to a foam. Trituration with ether gives 0.3 g. of off white solid [1(S),4S]-4-[4-[7-(aminosulfonyl)-6-chloro3,4-dihydro-1,1-dioxo-2H-1,2,4-benzothiadiazin-3-yl]phenoxy]-1-[3-(benzoylthio)-2-methyl-1-oxopropyl]-L-proline, methyl ester as a partial ether solvate and hydrate. Tlc (silica, $R_f$=0.5, hexane/acetate 2:1).

Anal Calc'd. for $C_{30}H_{31}N_4O_9S_3Cl \cdot 0.5\ C_4H_{10} \cdot 0.75H_2O$:
C, 49.70; H, 4.82; N, 7.24; S, 12.44;
Cl, 4.58.
Found: C, 49.73; H, 4.61; N, 7.34; S, 12.43;
Cl, 4.02.

(b)

[1(S),4S]-4-[4-[7-(Aminosulfonyl)-6-chloro-3,4-dihydro-1,1-dioxo-2H-1,2,4-benzothiadiazin-3-yl]phenoxy]-1-(3-mercapto-2-methyl-1-oxopropyl)-L-proline The product from part (a) (300 mg., 0.4 mmole) is hydrolyzed with 40 ml. of argon purged 0.2N sodium hydroxide at 25° for 1.5 hours. The mixture is acidified with potassium bisulfate to pH 1, then extracted with ethyl acetate (2×75 ml.), dried (Na$_2$SO$_4$) and evaporated to a foam. This is triturated with ether to give a white solid; Tlc (silica; dichloromethane (8), acetic acid (1), methanol (1)) $R_f$=0.9, 0.6 and 0.4 with the intermediate spot being most intense.

The mixture is chromatographed on 50 g. of Sephadex (LH 20 column, 25 mm diameter), by gravity, in methanol. The $R_f$=0.9 material eluted first followed by the R=0.6 and finally the $R_f$=0.4 material. The $R_f$=0.6 compound is homogeneous by Tlc. Evaporation and trituration gives 100 mg. of crystalline solid [1(S),4S]-4-[4-[7-(aminosulfonyl)-6-chloro-3,4-dihydro-1,1-dioxo-2H-1,2,4-benzothiadiazin-3-yl]phenoxy]-1-(3-mercapto-2-methyl-1-oxopropyl)-L-proline; m.p. 197°-199°.

Anal Calc'd. for $C_{22}H_{25}ClN_4O_8S_3 \cdot 0.5\ H_2O$:
C, 43.02; H, 4.27; N, 9.12; S, 15.66;
Cl, 5.77; SH, 5.38.
Found: C, 43.00; H, 4.33; N, 8.79; S, 15.27;
Cl, 5.50; SH, 5.16.

EXAMPLE 6

[1(S),4S]-4-[3-[7-(Aminosulfonyl)-6-chloro-3,4-dihydro-1,1-dioxo-2H-1,2,4-benzothiadiazin-3-yl]phenoxy]-1-(3-mercapto-2-methyl-1-oxopropyl)-L-proline (a)

[1(S),4S]-4-[3-[7-(Aminosulfonyl)-6-chloro-3,4-dihydro-1,1-dioxo-2H-1,2,4-benzothiadiazin-3-yl]phenoxy]-1-[3-(benzoylthio)-2-methyl-1-oxopropyl]-L-proline, methyl ester A mixture of 500 mg. (1.0 mmole) of [1(S),4S]-1-[3-(benzoylthio)-2-methyl-1-oxopropyl]-4-[3-(dimethoxymethyl)phenoxy]-L-proline, methyl ester and 280 mg. (1.0 mmole) of 4-amino-6-chloro-1,3-benzenedisulfonamide is refluxed in 30 ml. of acetonitrile with 1 mg. of p-toluenesulfonic acid for 24 hours. The solvent is removed in vacuo and the residue is triturated with ethyl ether. The resulting solid is filtered off and crystallized from ethyl acetate to yield 450 mg. of [1(S),4S]-4-[3-[7-(aminosulfonyl)-6-chloro-3,4-dihydro-1,1-dioxo-2H-1,2,4-benzothiadiazin-3-yl]phenoxy]-1-[3-(benzoylthio)-2-methyl-1-oxopropyl]-L-proline, methyl ester; m.p. 135° (dec.). Tlc (silica, dichloromethane) $R_f$=0.7.

Anal Calc'd. for $C_{30}H_{31}ClN_4O_9S_3 \cdot 0.5 CH_3COOC_2H_5$: C, 50.09; H, 4.60; N, 7.30; Cl, 4.62; S, 12.53.
Found: C, 50.09; H, 4.69; N, 7.39; Cl, 4.67; S, 12.36.

(b)

[1(S),4S]-4-[3-[7-(Aminosulfonyl)-6-chloro-3,4-dihydro-1,1-dioxo-2H-1,2,4-benzothiadiazin-3-yl]phenoxy]-1-(3-mercapto-2-methyl-1-oxopropyl)-L-proline To 720 mg. (1.0 mmole) of the product from part (a) under argon is added 40 ml. of 0.2N sodium hydroxide which has been purged for 2 hours with argon. The resulting solution is stirred for 4 hours at 25°, then acidified with potassium bisulfate. Extraction with ethyl acetate, drying ($Na_2SO_4$), and evaporation gives a foam. Trituration with ether gives 400 mg. of solid 3 spots on Tlc (silica; dichloromethane (8)/acetic acid (1)/methanol (1)). Chromatography on 50 g. of Sephadex (LH20) in methanol separates the product of intermediate polarity ($R_f$=0.6) as the second off the column. Evaporation gives a glass which yields 170 g. of white solid [1(S),4S]-4-[3-[7-(aminosulfonyl)-6-chloro-3,4-dihydro-1,1-dioxo-2H-1,2,4-benzothiadiazin-3-yl]phenoxy]-1-(3-mercapto-2-methyl-1-oxopropyl)-L-proline; m.p. 185°–188°. Trituration with ether gives an analytical sample.

Anal Calc'd. for $C_{22}H_{25}ClN_4O_8S_3.0.5H_2O$: C, 43.02; H, 4.27; N, 9.12; Cl, 5.77; S, 15.66; SH, 5.38. Found: C, 43.03; H, 4.27; N, 9.31; Cl, 5.83; S, 15.20; SH, 5.04.

EXAMPLE 7

[1(S),4S]-4-[3-[7-(Aminosulfonyl)-6-chloro-3,4-dihydro-1,1-dioxo-2H-1,2,4-benzothiadiazin-3-yl]phenoxy]-1-[3-(benzoylthio)-2-methyl-1-oxopropyl]-L-proline (a)

[1(S),4S]-1-[3-(Benzoylthio)-2-methyl-1-oxopropyl]-4-[3-(dimethoxymethyl)phenoxy]-L-proline, diphenylmethyl ester A mixture of 4.8 g. (9.5 mmole) of [1(S),4R]-1-[3-(benzoylthio)-2-methyl-1-oxopropyl]-4-hydroxy-L-proline, diphenylmethyl ester, 1.75 g. (1 eq.) of (3-dimethoxymethyl)phenol, and 2.73 g. (1 eq.) of triphenylphosphine in 30 ml. of dry tetrahydrofuran is stirred under argon at 0°. A solution of diethylazodicarboxylate (1.81 g./5 ml. of tetrahydrofuran) is added dropwise. After the addition is completed, the ice bath is removed and the reaction mixture is stirred at ambient temperature for 16 hours. Tlc of the reaction mixture shows a considerable amount of unreacted L-proline starting material. Therefore, an additional half equivalent of (3-dimethoxymethyl)phenol (0.88 g.), triphenylphosphine (1.37 g.) and diethylazodicarboxylate (0.9 g.) are added. After 25 hours no starting material remains.

The reaction mixture is concentrated to a residue. When the residue is slurried in petroleum ether:ether (1:1), an oil is formed. The liquid is decanted and saved. A solid forms which is filtered off and determined to be triphenylphosphine oxide. The combined solutions are concentrated to a residue.

This crude product is purified by repeated column chromatography. First, a flash chromatography on LPS silica eluting with a solvent gradient of hexane:ether (9:1 to 3:7) removes all of the dicarbethoxyhydrazine generated in the reaction and some non polar impurities. A gravity column on silica gel with an ethyl ether eluant removes the last traces of triphenylphosphine oxide. The two remaining compounds of very similar $R_f$'s are separated on a Waters Prep. LC (hexane:acetone, 4:1) giving 2.3 g. of pure [1(S),4S]-1-[3-(benzoylthio)-2-methyl-1-oxopropyl]-4-[3-(dimethoxymethyl)phenoxy]-L-proline, diphenylmethyl ester.

(b)

[1(S),4S]-4-[3-[7-(Aminosulfonyl)-6-chloro-3,4-dihydro-1,1-dioxo-2H-1,2,4-benzothiadiazin-3-yl]phenoxy]-1-[3-(benzoylthio)-2-methyl-1-oxopropyl]-L-proline A solution of 1.98 g. (3.03 mmole) of the product from part (a), 0.86 g. (1 eq.) of 4-amino-6-chloro-1,3-benzenedisulfonamide, 50 mg. of p-toluenesulfonic acid, and 3 ml. of anisole in 75 ml. of acetonitrile is refluxed overnight. After the solvent is evaporated, the residue is taken up in ethyl acetate and the product is extracted into 10% sodium bicarbonate. The aqueous layer is washed with ethyl acetate and acidified with 20% potassium bisulfate. The product is extracted into ethyl acetate. The organic phase is washed with water and brine, dried ($Na_2SO_4$), and evaporated to a solid. Trituration with dichloromethane removes most of a less polar impurity. Final purification on a Sephadex LH20 column eluting with methanol followed by evaporation of the solvent and trituration with ethyl ether gives [1(S),4S]-4-[3-[7-(aminosulfonyl)-6-chloro-3,4-dihydro-1,1-dioxo-2H-1,2,4-benzothiadiazin-3-yl]phenoxy]-1-[3-(benzoylthio)-2-methyl-1-oxopropyl]-L-proline as a white crystalline solid which is homogeneous by Tlc.

Anal Calc'd. for $C_{29}H_{29}ClN_4O_9S_3.1H_2O$: C, 47.89; H, 4.30; N, 7.70; S, 13.23; Cl, 4.87. Found: C, 47.98; H, 4.33; N, 7.70; S, 13.10; Cl, 4.90.

EXAMPLE 8

[1(S),4S]-4-[4-[7-(Aminosulfonyl)-6-chloro-3,4-dihydro-1,1-dioxo-2H-1,2,4-benzothiadiazin-3-yl]phenoxy]-1-[3-(benzoylthio)-2-methyl-1-oxopropyl]-L-proline A slurry of 1.0 g. (1.5 mmole) of [1(S),4S]-1-[3-(benzoylthio)-2-methyl-1-oxopropyl]-4-[4-(dimethoxymethyl)phenoxy]-L-proline, diphenylmethyl ester, 0.5 g. (1.75 mmole) of 4-amino-6-chloro-1,3-benzenedisulfonamide, 50 mg. of p-toluenesulfonic acid, and 1.5 ml. of anisole in 25 ml. of dry acetonitrile is refluxed for 5 hours, then evaporated to a foam. This is partitioned between ethyl acetate and dilute sodium bicarbonate. The aqueous phase is acidified and extracted with ethyl acetate. Drying ($Na_2SO_4$) and evaporation gives 0.6 g. of a tan foam, consisting of 3 components by Tlc [$R_f$=0.35, 0.5, 0.6 on silica; ethyl acetate (120), pyridine (20), acetic acid (6), water (1)]. Chromatography on 200 g. of Sephadex (LH20) in methanol affords on evaporation of the $R_f$=0.35 fractions and trituration with ether, 200 mg. of crystalline [1(S),4S]-4-[4-[7-(aminosulfonyl)-6-chloro-3,4-dihydro-1,1-dioxo-2H-1,2,4-benzothiadiazin-3-yl]phenoxy]-1-[3-(benzoylthio)-2-methyl-1-oxopropyl]-L-proline; m.p. 175°–185°.

Anal Calc'd. for $C_{29}H_{29}N_4O_9S_3Cl.0.5H_2O$: C, 48.50; H, 4.21; N, 7.80; S, 13.39; Cl, 4.94. Found: C, 48.39; H, 4.35; N, 7.62; S, 13.32; Cl, 4.95.

EXAMPLE 9

[1(S),4S]-4-[3-[6-(Aminosulfonyl)-7-chloro-1,2,3,4-tetrahydro-4-oxo-2-quinazolinyl]phenoxy]-1-[3-(benzoylthio)-2-methyl-1-oxopropyl]-L-proline A mixture of 1.7 g. (2.6 mmole) of [1(S),4S]-1-[3-(benzoylthio)-2-methyl-1-oxopropyl]-4-[3-(dimethoxymethyl)phenoxy]-L-proline, diphenylmethyl ester, 0.75 g. (3.0 mmole) of 2-amino-4-chloro-5-sulfamylbenzamide, 50 mg. of p-toluenesulfonic acid, and 3 ml. of anisole in 100 ml. of dry acetonitrile is refluxed for 2 hours, then evaporated and the residue shaken with ethyl acetate and aqueous sodium bicarbonate. A gummy solid formed, and 500 ml. of water is necessary for its solubilization. The organic layer is discarded and the aqueous layer is acidified with potassium bisulfate and extracted with ethyl acetate. The extracts are dried ($Na_2SO_4$) and evaporated to a solid with one major ($R_f$=0.32) and one minor ($R_f$=0.50) component by Tlc [silica; ethyl acetate (120), pyridine (20), acetic acid (6), water (11)].

Purification on a 200 g. Sephadex (LH 20) column in methanol gives, on evaporation and trituration with ether, 0.9 g. of white solid [1(S),4S]-4-[3-[6-(aminosulfonyl)-7-chloro-1,2,3-4-tetrahydro-4-oxo-2-quinazolinyl]phenoxy]-1-[3-(benzoylthio)-2-methyl-1-oxopropyl]-L-proline; m.p. 173°–178°, essentially homogeneous by Tlc.

Anal Calc'd. for $C_{30}H_{29}ClN_4O_8S_2.0.5H_2O$: C, 52.82; H, 4.43; N, 8.21; S, 9.40; Cl, 5.20. Found: C, 53.00; H, 4.54; N, 8.19; S, 9.46; Cl, 5.41.

EXAMPLE 10

[1(S),4S]-4-[2-[6-(Aminosulfonyl)-7-chloro-1,2,3,4-tetrahydro-4-oxo-2-quinazolinyl]phenoxy]-1-[3-(benzoylthio)-2-methyl-1-oxopropyl]-L-proline (a)

[1(S),4S]-1-[3-(Benzoylthio)-2-methyl-1-oxopropyl]-4-[2-(dimethoxymethyl)phenoxy]-L-proline, diphenylmethyl ester To a stirred mixture of 5.04 g. (0.01 mole) of [1(S),4R]-1-[3-(benzoylthio)-2-methyl-1-oxopropyl]-4-hydroxy-L-proline, diphenylmethyl ester, 2.52 g. (1.5 eq.) of 2-(dimethoxymethyl)phenol, and 3.93 g. (1.5 eq.) of triphenylphosphine in 15 ml. of dry tetrahydrofuran under argon at 0° is added dropwise a solution of 2.61 g. (1.5 eq.) of diethylazodicarboxylate in 5 ml. of tetrahydrofuran. The reaction mixture is stirred at ambient temperature for approximately 20 hours. The reaction mixture is concentrated to a residue and chromatographed twice [silica gel gravity column (ethyl ether eluent) and LPS-1 silica (hexane:acetone, 4:1)] yielding [1(S),4S]-1-[3-(benzoylthio)-2-methyl-1-oxopropyl]-4-[2-(dimethoxymethyl)phenoxy]-L-proline, diphenylmethyl ester.

(b)

[1(S),4S]-4-[2-[6-(Aminosulfonyl-7-chloro-1,2,3,4-tetrahydro-4-oxo-2-quinazolinyl]phenoxy]-1-[3-(benzoylthio)-2-methyl-1-oxopropyl]-L-proline 1 g. (1.5 mmole) of the product from part (a), 0.5 g. (2 mmole) of 2-amino-4-chloro-5-sulfamylbenzamide and 2 ml. of anisole are combined in 15 ml. of acetonitrile. A catalytic amount of p-toluenesulfonic acid (50 mg.) is added and the reaction mixture is refluxed for 2 hours. After concentrating to a residue, the reaction mixture is dissolved in ethyl acetate and water. The aqueous layer is discarded and the product is extracted into a sodium bicarbonate solution. After washing with ethyl acetate, the aqueous phase is acidified with potassium bisulfate and the product is extracted with ethyl acetate. The ethyl acetate solution was washed with water and brine and dried (MgSO4). The solvent is evaporated to give a white solid which is purified on a Sephadex (LH20) column. Trituration of the chromatographed product gives [1(S),4S]-4-[2-[6-(aminosulfonyl)-7-chloro-1,2,3,4-tetrahydro-4-oxo-2-quinazolinyl]phenoxy]-1-[3-(benzoylthio)-2-methyl-1-oxopropyl]-L-proline; m.p. 190°–205°, as a white crystalline solid.

Anal Calc'd. for $C_{30}H_{29}ClN_4O_8S_2.0.38H_2O$: C, 52.99; H, 4.41; N, 8.24; S, 9.43; Cl, 5.21. Found: C, 52.99; H, 4.43; N, 8.12; S, 9.08; Cl, 5.28.

EXAMPLE 11

(cis)-4-[3-[6-(Aminosulfonyl)-7-chloro-1,2,3,4-tetrahydro-4-oxo-2-quinazolinyl]phenoxy]-1-[[(3-ethoxy-3-oxopropyl)ethylamino]carbonyl]-L-proline (a)

(trans)-1-[(1,1-Dimethylethoxy)carbonyl]-4-hydroxy-L-proline

To a solution of 20 g. (153 mmole) of (trans)-4-hydroxy-L-proline in 150 ml. of aqueous acetone is added triethylamine (32 ml., 1.5 eq.) followed by 2-(tert-butoxycarbonyloxyimino)-2-phenylacetonitrile (41.3 g., 1.1 eq.) and the resulting solution is stirred at room temperature. After 18 hours, the solution is diluted with water and extracted twice with ether. The ether fractions are discarded. The aqueous layer is acidified with 300 ml. of 0.5M citric acid and extracted four times with ethyl acetate. The organic fractions are combined and washed with water and brine. After drying (Na2SO4), the solvent is removed at reduced pressure to give 26.55 g. of (trans)-1-[(1,1-dimethylethoxy)carbonyl]-4-hydroxy-L-proline as a pale yellow oil. $R_f$(silica gel, dichloromethane/methanol/acetic acid; 18:1:1)=0.64.

(b)

(trans)-1-[(1,1-Dimethylethoxy)carbonyl]-4-(1,3-dioxobutoxy)-L-proline

To a suspension of 13 g. (56 mmole) of (trans)-1-[(1,1-dimethylethoxy)carbonyl]-4-hydroxy-L-proline in 100 ml. of anhydrous dichloromethane under argon is added triethylamine (7.81 ml., 1 eq.). To the resulting clear solution is added distilled diketene (4.39 ml., (1 eq.) and the solution darkened. After stirring at room temperature for 3.5 hours, the solvent is removed at reduced pressure. The residue is dissolved in ethyl acetate and washed with 1M hydrochloric acid (60 ml.) and water. After drying (Na2SO4), the solvent is removed at reduced pressure to give 13.92 g. of (trans)-1-[(1,1-dimethylethoxy)carbonyl]-4-(1,3-dioxobutoxy)-L-proline as a yellow oil. $R_f$(silica gel, dichloromethane/methanol/acetic acid; 8:1:1)=0.58, secondary spot at $R_f$=0.7.

(c)

(trans)-1-[1,1-(Dimethylethoxy)carbonyl]-4-(1,3-dioxobutoxy)-L-proline, phenylmethyl ester To a solution of 13.92 g. (44 mmole) of (trans)-1-[(1,1-dimethylethoxy)carbonyl]-4-(1,3-dioxobutoxy)-L-proline in 100 ml. of dimethylformamide (distilled in glass) under argon is added sodium bicarbonate (7.39 g., 2 eq.) followed by benzyl bromide (26.17 ml., 5 eq.). The resulting solution is stirred for 24 hours at room temperature. The solution is diluted with water and extracted three times with ether. The ether extracts are combined and washed with water, 1N sodium bicarbonate (twice), water, and brine. After drying (MgSO4), the solvent is removed at reduced pressure to give 38.79 g. of crude (trans)-1-[(1,1-dimethylethoxy)carbonyl]-4-(1,3-dioxobutoxy)-L-proline, phenylmethyl ester as a yellow oil. $R_f$ (silica gel, ethyl acetate)=0.61, secondary spots at $R_f$=0.13, 0.45, 0.65.

(d)

(trans)-1-[(1,1-Dimethethoxy)carbonyl]-4-hydroxy-L-proline, phenylmethyl ester

To a solution of the crude (trans)-1-[(1,1-dimethylethoxy)carbonyl]-4-(1,3-dioxobutoxy)-L-proline, phenylmethyl ester (34.79 g.) in 500 ml. of isopropanol is added a solution of hydrazine hydrate (3.83 ml., 2 eq.) in 50 ml. of isopropanol. The resulting solution is stirred under argon for four hours. The solvent is removed at reduced pressure and the residue taken up in ethyl acetate. This is washed with water (twice), ice cold 1N hydrochloric acid, 1N sodium bicarbonate and brine. After drying (MgSO$_4$), the solvent is removed at reduced pressure. The residue is flash chromatographed (Whatman silica gel LPS-1, ethyl acetate:hexane, 6:4) to give 9.53 g. of (trans)-1-[(1,1-dimethylethoxy)carbonyl]-4-hydroxy-L-proline, phenylmethyl ester as a pale yellow oil, R$_f$(silica gel, ethyl acetate)=0.45.

(e) (trans)-4-Hydroxy-L-proline, phenylmethyl ester, p-toluenesulfonic acid salt 75 ml. of cold (0°) trifluoroacetic acid is added to (trans)-1-[(1,1-dimethylethoxy)carbonyl]-4-hydroxy-L-proline, phenylmethyl ester (9.5 g., 29.56 mmole) and the resulting solution is stirred at 0° for one hour. The solvent is removed at reduced pressure. Toluene is added and the solution is concentrated once more. The residue is dissolved in ether and to it is added a solution of p-toluenesulfonic acid (5.62 g., 1 eq.) in ether. A precipitate slowly forms. This is filtered and washed with ether to give 9.33 g. of (trans)-4-hydroxy-L-proline, phenylmethyl ester, p-toluenesulfonic acid salt as a white solid; m.p. 120°–124°.

(f) 3-(Ethylamino)propanoic acid, ethyl ester

Into 200 ml. of cold (−60°) absolute ethanol is passed anhydrous ethylamine (36 g., 781 mmole, 1.1 eq.). To the resulting ethanolic solution is added dropwise a solution of ethyl acrylate (71 g., 710 mmole, 1 eq.) in 150 ml. of absolute ethanol over a period of several hours. The resulting mixture is then stirred at −60° for 0.5 hours and allowed to warm slowly to room temperature where it is stirred for another 20 hours. The solvent is removed at reduced pressure to give 33 g. of 3-(ethylamino)propanoic acid, ethyl ester as colorless liquid; b.p. 80°–83°.

(g) (trans)-1-[[(3-Ethoxy-3-oxopropyl)ethylamino]carbonyl]-4-hydroxy-L-proline, phenylmethyl ester To a cold (−30°) solution of 1.25M phosgene in benzene (25.52 ml., 1.5 eq.) in 20 ml. of anhydrous dichloromethane under argon is added dropwise a solution of 3-(ethylamino)propanoic acid, ethyl ester (3.09 g., 21.26 mmole) and N-methylmorpholine (3.5 ml., 1.5 eq.) in 20 ml. of dichloromethane. The resulting mixture is stirred for one hour at −30° and then for one hour at room temperature. The solvent is removed at reduced pressure. Additional dichloromethane is added and the solution is concentrated once more.

This residue is dissolved in 30 ml. of dichloromethane and (trans)-4-hydroxy-L-proline, phenylmethyl ester, p-toluenesulfonic acid salt (10.5 g., 1.2 eq.) is added. To the resulting suspension is added dropwise N-methylmorpholine (5.6 ml., 2.4 eq.) in 20 ml. of dichloromethane. The resulting mixture is stirred at room temperature for 15 hours. The solvent is removed at reduced pressure and the residue taken up in ethyl acetate. This is washed with water (twice), 1N hydrochloric acid (twice), 1N sodium bicarbonate (twice), and once with brine. After drying (MgSO$_4$), the solvent is removed at reduced pressure. The residue is flash chromatographed (Whatman silica gel LPS-1, hexane:ethyl acetate; 65:35) to give 7.72 g. of (trans)-1-[[(3-ethoxy-3-oxopropyl)ethylamino]carbonyl]-4-hydroxy-L-proline, phenylmethyl ester as a colorless oil, R$_f$(silica gel, ethyl acetate)=0.34.

(h) (cis)-4-[3-(Dimethoxymethyl)phenoxy]-1-[[(3-ethoxy-3-oxopropyl)ethylamino]carbonyl]-L-proline, phenylmethyl ester To a cold (0°) solution of 3-(dimethoxymethyl)phenol (4.96 g., 1.5 eq.), (trans)-1-[[(3-ethoxy-3-oxopropyl)ethylamino]carbonyl]-4-hydroxy-L-proline, phenylmethyl ester (7.72 g., 19.67 mmole), and triphenylphosphine (7.74 g., 1.5 eq.) in 100 ml. of anhydrous tetrahydrofuran under argon is added dropwise a solution of diethylazodicarboxylate in 20 ml. of tetrahydrofuran. Following the addition, the solution is stirred for one hour at 0° and for 18 hours at room temperature thereafter. The solution is diluted with ether and filtered. The filtrate is washed twice with water and dried (MgSO$_4$) The solvent is removed at reduced pressure. The residue is flash chromatographed (Whatman silica gel LPS-1; hexane:acetone; 7:3) and the resulting product is taken up in about 100 ml. of a 1:1 solution of petroleum ether and ether and allowed to stand overnight under refrigeration. The solution is filtered through glass wool and the solvent is removed at reduced pressure. The residue is taken up in benzene and run through the Waters Prep liquid chromatography system (hexane:acetone, 4:1) to give 3.11 g. of (cis)-4-[3-(dimethoxymethyl)phenoxy]-1-[[(3-ethoxy-3-oxopropyl)ethylamino]carbonyl]-L-proline, phenylmethyl ester as a clear oil, R$_f$(silica gel, hexane:acetone; 1:1)=0.36.

(i) (cis)-4-[3-[6-(Aminosulfonyl)-7-chloro-1,2,3,4-tetrahydro-4-oxo-2-quinazolinyl]phenoxy]-1-[[(3-ethoxy-3-oxopropyl)ethylamino]carbonyl]-L-proline, phenylmethyl ester A mixture of (cis)-4-[3-(dimethoxymethyl)phenoxy]-1-[[(3-ethoxy-3-oxopropyl)ethylamino]carbonyl]-L-proline, phenylmethyl ester (700 mg., 1.29 mmole), 2-amino-4-chloro-5-sulfamylbenzamide (290 mg., 1.16 mmole) and approximately 10 mg. of aqueous p-toluenesulfonic acid in 12 ml. of dry acetonitrile is heated at reflux. After 75 minutes the mixture is cooled, solvent removed at reduced pressure and the residue treated with ether to yield a crystalline solid. This material is flash chromatographed on silica gel eluted with hexane:acetone (4:6) and approximately 50 ml. fractions are collected.

Fractions #27–40 are combined and concentrated to give 790 mg. of (cis)-4-[3-[6-(aminosulfonyl)-7-chloro-1,2,3,4-tetrahydro-4-oxo-2-quinazolinyl]phenoxy]-1-[[(3-ethoxy-3-oxopropyl)ethylamino]carbonyl]-L-proline, phenylmethyl ester.

(j) (cis)-4-[3-[6-(Aminosulfonyl)-7-chloro-1,2,3,4-tetrahydro-4-oxo-2-quinazolinyl]phenoxy]-1-[[(3-ethoxy-3-oxopropyl)ethylamino]carbonyl]-L-proline To a solution of the phenylmethyl ester product of part (i) (505 mg., 0.69 mmole) in 40 ml. of absolute ethanol is added approximately 70 mg. of 10% palladium on charcoal. The resulting mixture is stirred under hydrogen for approximately 2.5 hours at which time Tlc analysis shows no starting material remaining. The mixture is filtered and concentrated at reduced pressure to give a pale gray foam which is dried under vacuum overnight to give 430 mg. of material. In order to remove additional palladium/charcoal, this material is dissolved in ethanol, millipore filtered, and concentrated at reduced pressure. The residue is dissolved in tetrahydrofuran, precipitated with ether to give a white solid, and dried overnight under vacuum to give (cis)-4-[3-[6-(aminosulfonyl)-7-chloro-1,2,3,4-tetrahydro-4-oxo-2-quinazolinyl]phenoxy]-1-[[(3-ethoxy-3-oxopropyl)ethylamino]carbonyl]-L-proline.

Anal. calc'd. for $C_{27}H_{32}N_5O_9SCl.0.5H_2O$: C, 50.11; H, 5.14; N, 10.82; S, 4.95; Cl, 5.48. Found: C, 50.06; H, 5.22; N, 10.51; S, 4.98; Cl, 5.41.

EXAMPLE 12

(cis)-4-[3-[6-(Aminosulfonyl)-7-chloro-1,2,3,4-tetrahydro-4-oxo-2-quinazolinyl]phenoxy]-1-[[(2-carboxyethyl)ethylamino]carbonyl]-L-proline The product from Example 11 is dissolved in aqueous tetrahydrofuran and treated with a molar excess of aqueous sodium hydroxide. After the reaction is complete, the solution is acidified with dilute hydrochloric acid to precipitate out (cis)-4-[3-[6-(aminosulfonyl)-7-chloro-1,2,3,4-tetrahysro-4-oxo-2-quinazolinyl]phenoxy]-1-[[(2-carboxyethyl)ethylamino]carbonyl]-L-proline.

EXAMPLE 13

[1(S),4S]-4-[4-[7-(Aminosulfonyl)-3,4-dihydro-1,1-dioxo-6-(trifluoromethyl)-2H-1,2,4-benzothiadiazin-3-yl]phenoxy]-1-[3-(benzoylthio)-2-methyl-1-oxopropyl]-L-proline To a mixture of [1(S),4S]-1-[3-(benzoylthio)-2-methyl-1-oxopropyl]-4-[4-(dimethoxymethyl)phenoxy]-L-proline, diphenylmethyl ester (3.5 g., 5.35 mmole), 4-amino-6-trifluoromethyl-1,3-benzenedisulfonamide (1.75 g.) and anisole (3.5 ml.) in 80 ml. acetonitrile is added p-toluenesulfonic acid (120 mg.). The reaction mixture is refluxed for 17 hours. After concentrating to a residue and triturating with dichloromethane, the crude solid is flash chromatographed on LPS-1 silica eluting with ethyl acetate:pyridine:acetic acid:water (2400:50:15:27). The fractions containing the pure product are combined and concentrated. Further purification is achieved on an LH-20 column eluting with methanol to give white solid [1(S),4S]-4-[4-[7-(aminosulfonyl)-3,4-dihydro-1,1-dioxo-6-(trifluoromethyl)-2H-1,2,4-benzothiadiazin-3-yl]phenoxy]-1-[3-(benzoylthio)-2-methyl-1-oxopropyl]-L-proline; m.p. 160° (foams); $[\alpha]_D = -27°$ (c=1, methanol). $R_f$ (silica gel, dichloromethane/methanol/acetic acid; 8:1:1) = 0.42.

Anal. calc'd. for $C_{30}H_{29}F_3N_4O_9S_3.1H_2O..0.7C_2H_5OC_2H_5$: C, 48.77; H, 4.53; N, 6.89; S, 11.83; F, 7.01. Found: C, 48.36; H, 4.27; N, 7.15; S, 11.79; F, 7.50.

EXAMPLE 14

[1(S),4S]-4-[3-[7-(Aminosulfonyl)-3,4-dihydro-1,1-dioxo-6-(trifluoromethyl)-2H-1,2,4-benzothiadiazin-3-yl]phenoxy]-1-[3-(benzoylthio)-2-methyl-1-oxopropyl]-L-proline To a mixture of [1(S),4S]-1-[3-(benzoylthio)-2-methyl-1-oxopropyl]-4-[3-(dimethoxymethyl)phenoxy]-L-proline, diphenylmethyl ester (6.0 g., 9 mmole), 4-amino-6-trifluoromethyl-1,3-benzenedisulfonamide (3 g., 10 mmole) and anisole (3 ml.) in 150 ml. of acetonitrile is added p-toluenesulfonic acid (100 mg.). The mixture is refluxed for 12 hours. After evaporating to an oil, the crude product is taken up in ethyl acetate, washed with water, dried ($Na_2SO_4$), and evaporated to a solid. The product is flash chromatographed on LPS-1 silica eluting with ethyl acetate:pyridine:acetic acid:water (2400:50:13:27). The fractions containing the pure product are combined and concentrated. Further purification is achieved on an LH-20 column eluting with methanol to give white solid [1(S),4S]-4-[3-[7-(aminosulfonyl)-3,4-dihydro-1,1-dioxo-6-(trifluoromethyl)-2H-1,2,4-benzothiadiazin-3-yl]phenoxy]-1-[3-(benzoylthio)-2-methyl-1-oxopropyl]-L-proline; m.p. 175°–178° (foams); $[\alpha]_D = -30.4°$ (c=1.0, methanol). $R_f$ (silica gel; dichloromethane:methanol:acetic acid; 8:1:1) = 0.45.

Anal. calc'd. for $C_{30}H_{29}F_3N_4O_9S_3$: C, 48.51; H, 3.94; N, 7.54; S, 12.95; F, 7.67. Found: C, 48.54; H, 4.13; N, 7.23; S, 12.69; F, 7.50.

EXAMPLE 15

[1(S),4S]-4-[4-[7-(Aminosulfonyl)-6-chloro-3,4-dihydro-2-methyl-1,1-dioxo-2H-1,2,4-benzothiadiazin-3-yl]phenoxy]-1-[3-(benzoylthio)-2-methyl-1-oxopropyl]-L-proline (a)

[1(S),4S]-1-[3-(Benzoylthio)-2-methyl-1-oxopropyl]-4-(4-formylphenoxy)-L-proline A mixture of [1(S),4R]-1-[3-(benzoylthio)-2-methyl-1-oxopropyl]-4-hydroxy-L-proline, diphenylmethyl ester (10 g., 20 mmole), 4-hydroxybenzaldehyde (2.4 g., 20 mmole), and triphenylphosphine (5.2 g., 20 mmole) in benzene (150 ml.) is evaporated to dryness, then taken up in dry, freshely distilled tetrahydrofuran (100 ml.), cooled to −8° and treated with diethylazodicarboxylate (3.6 g., 20 mmole). After 15 minutes the cooling bath is replaced with a cold water bath and the temperature is raised to 50°–52° over 2 hours and is held there for another 2 hours, before allowing it to come to 25° overnight. The oil obtained on evaporation is taken in dichloromethane (100 ml.), treated with trifluoroacetic acid (50 ml.), and allowed to stand at 25° for 3 hours. The volatiles are evaporated and toluene is added and evaporated. This treatment is repeated twice to give an oil with no acidic odor. This material is taken up in ethyl acetate and extracted with saturated sodium bicarbonate (2×75 ml.). The aqueous fraction is washed with ethyl acetate, acidified with concentrated hydrochloric acid, extracted with ethyl acetate (500 ml.), dried ($Na_2SO_4$), and evaporated to give 11 g. of viscous oil containing product and deprotected starting material. Most of the latter impurity is removed by slurrying in dichloromethane (300 ml.) and filtering. The filtrates are applied to an 800 g. silica (60–200 mesh) dry column and eluted with acetone. The eluant is somewhat colored. It is evaporated and the resultant oil is taken up in ethyl acetate (200 ml.) and treated with excess dicyclohexylamine. After standing undisturbed for 3 hours, the yellow solution is decanted and the residual solid is washed with more solvent, filtered, and dried to give 6 g. of beige [1(S),4S]-1-[3-(benzoylthio)-2-methyl-1-oxopropyl]-4-(4-formylphenoxy)-L-proline, dicyclohexylamine salt.

This salt product is shaken with 10% potassium bisulfate and ethyl acetate, the organic layer is dried and evaporated to a tan foam. This material is covered with a small volume of ethyl acetate and scratched. The resulting white solid is filtered, washed with a small volume of cold ethyl acetate, then with hexane, dried at 55° in vacuo for 5 fours to give 1.8 g. of white solid [1(S),4S]-1-[3-(benzoylthio)-2-methyl-1-oxopropyl]-4-

(4-formylphenoxy)-L-proline; m.p. 138°–140°; $[\alpha]_D = -35.8°$ (c=1.0, methanol). $R_f$ (silica gel; dichloromethane:methanol; 4:1)=0.6.

Anal. calc'd. for $C_{23}H_{23}NO_6S$: C, 62.57; H, 5.25; N, 3.17; S, 7.26. Found: C, 62.30; H, 5.34; N, 3.13; S, 7.03.

(b)
4-Amino-6-chloro-$N^3$-methyl-1,3-benzenedisulfonamide

A mixture of 4-amino-6-chloro-1,3-benzenedisulfonamide (30 g., 105 mmole) and urea (12.6 g., 210 mmole) are ground together and then heated in a 200°–205° oil bath. Within 30 minutes the sample is a molten foam, which in another 30 minutes resolidifies. After a further 30 minutes heating, the flask is cooled and the contents slurried in water and acidified. The cream-colored powder is filtered, washed with water, and dried azeotropically with benzene to yield 31 g. of 6-chloro-3,4-dihydro-3-oxo-2H-1,2,4-benzothiadiazine-7-sulfonamide, 1,1-dioxide.

Under argon, this 6-chloro-3,4-dihydro-3-oxo-2H-1,2,4-benzothiadiazine-7-sulfonamide, 1,1-dioxide (10 g., 30 mmole) is dissolved in dimethylformamide (25 ml.) at 60°–65°. To this is added 1 equivalent of sodium hydride (60% in mineral oil, 1.24 g., 30 mmole) in portions. After heating and stirring for 15 minutes, methyl iodide (4.2 g., 30 mmole) is dripped in over 5 minutes. The mixture is then heated at 60°–65° for one hour. The mixture is cooled somewhat and added to cold water (800 ml.), giving beige crystals and a yellow aqueous material. The solid is washed with water and air-dried to give 9.2 g. of 6-chloro-3,4-dihydro-2-methyl-3-oxo-2H-1,2,4-benzothiadiazepin-7-sulfonamide, 1,1-dioxide.

The above 6-chloro-3,4-dihydro-2-methyl-3-oxo-2H-1,2,4-benzothiadiazine-7-sulfonamide, 1,1-dioxide (9.2 g., 28 mmole) is dissolved in 20% sodium hydroxide (90 ml.) and refluxed overnight in a 120°–140° oil bath. The clear solution goes from brown to yellow. The mixture is diluted with water (350 ml.) and extracted with hexane. The aqueous phase is acidified with concentrated hydrochloric acid and chilled at 5° for 36 hours. The resulting beige solid is filtered, washed with water, and dried azeotropically with benzene to give 8.0 g. of crude product. Recrystallization of 6 g. of this material from ethanol (100 ml.) and water (200 ml.) gives 4g. of 4-amino-6-chloro-$N^3$-methyl-1,3-benzenedisulfonamide as off-white crystals; m.p. 168°–170°. [Literature m.p. 168°–169°, *JACS*, Vol. 82, p. 1132 (1960)].

(c)
[1(S),4S]-4-[4-[7-(Aminosulfonyl)-6-chloro-3,4-dihydro-2-methyl-1,1-dioxo-2H-1,2,4-benzothiadiazin-3-yl]phenoxy]-1-[3-(benzoylthio)-2-methyl-1-oxopropyl]-L-proline A mixture of [1(S),4S]-1-[3-(benzoylthio)-2-methyl-1-oxopropyl]-4-(4-formylphenoxy)-L-proline (1.5 g., 3.4 mmole) and 4-amino-6-chloro-$N^3$-methyl-1,3-benzenedisulfonamide (1.02 g., 3.4 mmole) in acetonitrile (200 ml.) is treated with 50 mg. of p-toluenesulfonic acid and distilled to a final volume of 50 ml., in portions, over 36 hours. Evaporation gives a foam which is insoluble in ethyl acetate. Chromatography on 200 g. of LH-20 Sephadex in methanol removes the color but gives incomplete separation of product from reactants. The product containing fractions are pooled, evaporated and chromatographed on 800 g. silica (60–200 mesh) column in ethyl acetate (360), pyridine (20), water (11), and acetic acid (6). Pooling of the product containing fractions gives a gum. This is taken up in methanol and chromatographed on 200 g. LH-20. Product containing fractions are pooled and evaporated to a glass. Trituration with ether gives 0.3 g. of off-white solid [1(S),4S]-4-[4-[7-(aminosulfonyl)-6-chloro-3,4-dihydro-2-methyl-1,1-dioxo-2H-1,2,4-benzothiadiazin-3-yl]phenoxy]-1-[3-(benzoylthio)-2-methyl-1-oxopropyl]-L-proline; m.p. 178°–184°; $[\alpha]_D = -25°$ (c=0.1, methanol). Drying in vacuo gives an analytical sample. $R_f$ (silica; dichloromethane:methanol:acetic acid; 8:1:1)=0.43.

Anal. calc'd. for $C_{30}H_{31}ClN_4O_9S_3 \cdot 1.0H_2O$ C, 48.61; H, 4.49; N, 7.56; S, 12.98; Cl, 4.78. Found: C, 49.00; H, 4.45; N, 7.35; S, 13.05; Cl, 4.71.

EXAMPLES 16–28

Following the procedures of Examples 1 to 10 and 13 to 15 the dimethoxymethyl or formyl substituted phenoxy proline ester of Col. I is reacted with the substituted benzenamine shown in Col. II to yield the ester product of Col. III. If R is methyl, treatment with sodium hydroxide as described in Examples 1 to 3, 5 and 6 yields the mercaptoalkanoyl-L-proline shown in Col. IV. If R is benzhydryl, treatment with p-toluenesulfonic acid and anisole yields the acylmercaptoalkanoyl-L-proline shown in Col. V

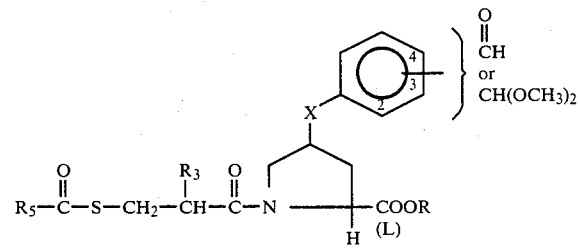

Col. I

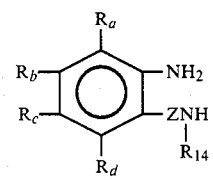

Col. II

-continued
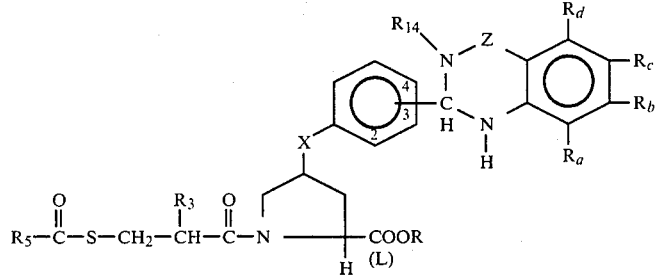
Col. III
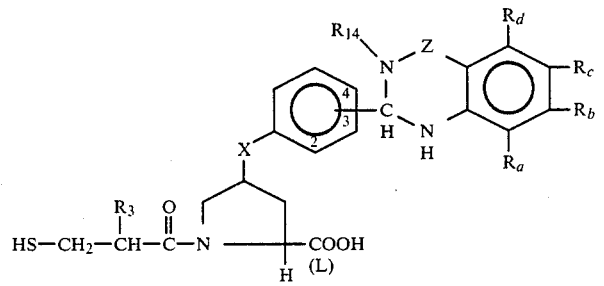
Col. IV
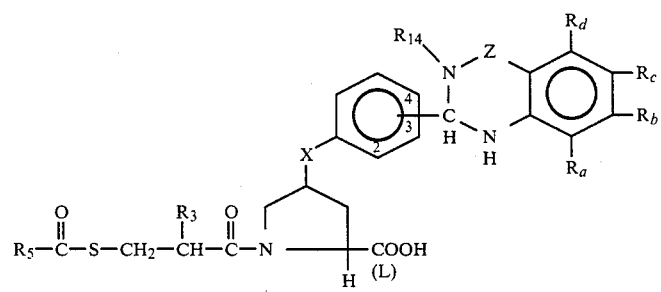
Col. V
| Example | X | R₅ | R₃ | R |
|---|---|---|---|---|
| 16 | O | H₃C— | H₃C— | —CH₃ |
| 17 | S | H₃C— | H₃C— | —CH(C₆H₅)₂ |
| 18 | O | H₃C— | H₃C— | —CH(C₆H₅)₂ |
| 19 | S | 2-thienyl | H— | —CH(C₆H₅)₂ |
| 20 | O | 2-thienyl | H₅C₂— | —CH₃ |
| 21 | O | 2-thienyl | H₃C— | —CH(C₆H₅)₂ |

-continued

| | | | | | |
|---|---|---|---|---|---|
| 22 | O | [benzyl: C₆H₅-CH₂-] | F₃C | —CH₃ | |
| 23 | O | [4-methoxyphenyl-methyl: H₃CO-C₆H₄-] | H₃C— | —CH₃ | |
| 24 | O | [4-chlorophenyl-methyl: Cl-C₆H₄-] | H₃C— | —CH(C₆H₅)₂ | |
| 25 | S | H₅C₂— | H₃C— | —CH₃ | |
| 26 | O | [furan-2-yl-methyl] | H₃C— | —CH₃ | |
| 27 | O | [2-(pyridin-3-yl)ethyl: Pyr-(CH₂)₂-] | H₃C— | —CH(C₆H₅)₂ | |
| 28 | O | [(pyridin-4-yl)methyl] | H₃C— | —CH(C₆H₅)₂ | |

| Example | position | $R_a$ | $R_b$ | $R_c$ | $R_d$ | $R_{14}$ | Z |
|---|---|---|---|---|---|---|---|
| 16 | 2- | H | Cl | SO₂NH₂ | H | H | CO |
| 17 | 3- | H | Cl | SO₂NH₂ | H | H | CO |
| 18 | 4- | H | Cl | SO₂NH₂ | H | —CH₂—C₆H₅ | SO₂ |
| 19 | 2- | H | H | H | H | H | SO₂ |
| 20 | 3- | H₃C | H | H | H | H | CO |
| 21 | 4- | H | OC₂H₅ | SO₂NH₂ | H | H | SO₂ |
| 22 | 2- | H | Cl | SO₂NH₂ | H | —CH₃ | SO₂ |
| 23 | 3- | H | CF₃ | NO₂ | H | H | CO |
| 24 | 4- | H | Cl | NO₂ | H | H | CO |
| 25 | 2- | H | SO₂NH₂ | Cl | H | —CH₃ | SO₂ |
| 26 | 3- | Cl | H | H | SO₂NH₂ | H | CO |
| 27 | 4- | H | Br | SO₂NH₂ | H | H | CO |
| 28 | 2- | H | NO₂ | SO₂NH₂ | H | H | SO₂ |

EXAMPLES 29–40

Following the procedure of Example 11 but employing the dimethoxymethyl or formyl substituted proline ester of Col. I and the substituted benzenamine shown in Col. II one obtains the L-proline ester product shown in Col. III which is then hydrogenated to the product shown in Col. IV.

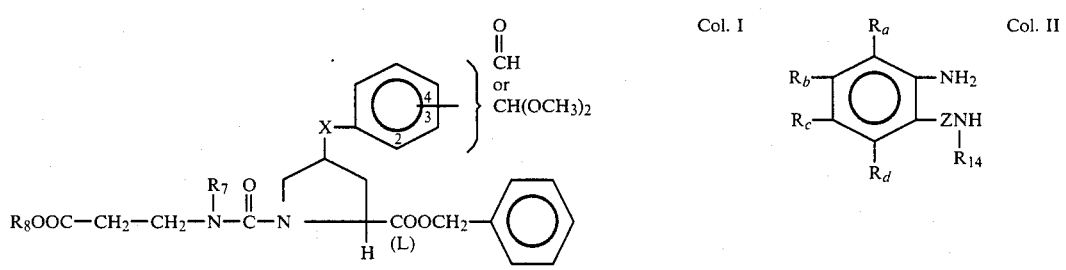

-continued

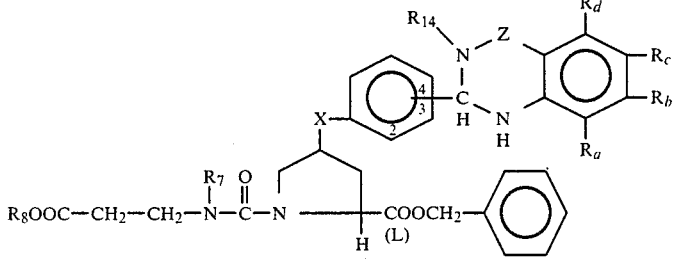
Col. III

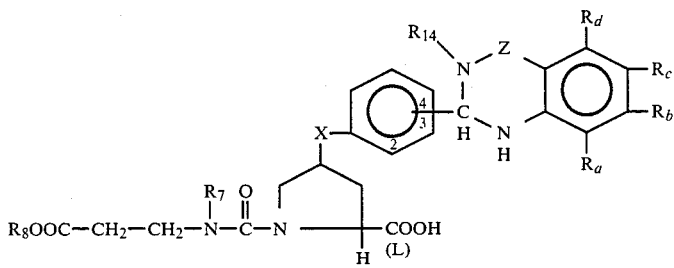
Col. IV

| Example | X | R$_8$ | R$_7$ | position | R$_a$ | R$_b$ | R$_c$ | R$_d$ | Z | R$_{14}$ |
|---|---|---|---|---|---|---|---|---|---|---|
| 29 | O | H$_5$C$_2$— | H$_5$C$_2$— | 2- | H | Cl | SO$_2$NH$_2$ | H | CO | —CH$_3$ |
| 30 | S | H$_5$C$_2$— | H$_5$C$_2$— | 4- | H | Cl | SO$_2$NH$_2$ | H | CO | H |
| 31 | O | H$_5$C$_2$— | H$_5$C$_2$— | 2- | H | Cl | SO$_2$NH$_2$ | H | SO$_2$ | H |
| 32 | S | H$_5$C$_2$— | H$_5$C$_2$— | 3- | H | Cl | SO$_2$NH$_2$ | H | SO$_2$ | —CH$_3$ |
| 33 | O | H$_5$C$_2$— | H$_5$C$_2$— | 4- | H | Cl | SO$_2$NH$_2$ | H | SO$_2$ | H |
| 34 | O | H$_5$C$_2$— | H$_3$C— | 2- | H | H | H | H | CO | H |
| 35 | S | H$_5$C$_2$— | (H$_3$C)$_2$—HC— | 3- | CH$_3$ | H | SO$_2$NH$_2$ | H | SO$_2$ | H |
| 36 | O | H$_5$C$_2$— | H$_9$C$_4$— | 4- | H | OC$_2$H$_5$ | Cl | H | CO | —CH$_2$—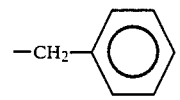 |
| 37 | O | H$_5$C$_2$— | H$_5$C$_2$— | 2- | H | H | SO$_2$NH$_2$ | Cl | SO$_2$ | H |
| 38 | O | H$_7$C$_3$— | H$_5$C$_2$— | 3- | H | Br | SO$_2$NH$_2$ | H | CO | H |
| 39 | O | H$_5$C$_2$— | H$_5$C$_2$— | 4- | H | CF$_3$ | SO$_2$NH$_2$ | H | SO$_2$ | H |
| 40 | O | H$_3$C— | H$_5$C$_2$— | 3- | H | CH$_2$CCl$_3$ | SO$_2$NH$_2$ | H | CO | H |

EXAMPLE 41

1000 tablets each containing the following ingredients:

| | |
|---|---|
| [1(S),4S]—4-[3-[6-(Amino-sulfonyl)-7-chloro-1,2,3,4-tetrahydro-4-oxo-2-quinazolinyl]phenoxy]-1-(3-mercapto-2-methyl-1-oxopropyl)-L-proline | 100 mg. |
| Corn starch | 50 mg. |
| Gelatin | 7.5 mg. |
| Avicel (microcrystalline cellulose) | 25 mg. |
| Magnesium stearate | 2.5 mg. |
| | 185 mg. | are prepared from sufficient bulk quantitites by mixing the [1(S),4S]-4-[3-[6-(aminosulfonyl)-7-chloro-1,2,3,4-tetrahydro-4-oxo-2-quinazolinyl]phenoxy]-1-(3-mercapto-2-methyl-1-oxopropyl)-L-proline and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 2 to 40 can be prepared.

EXAMPLE 42

Two-piece #1 gelatin capsules each containing 100 mg. of (cis)-4-[3-[6-(aminosulfonyl)-7-chloro-1,2,3,4-tetrahydro-4-oxo-2-quinazolinyl]phenoxy]-1-[[(3-hydroxy-3-oxopropyl)ethylamino]carbonyl]-L-proline are filled with a mixture of the following ingredients:

| | |
|---|---|
| (cis)-4-[3-[6-(Amino-sulfonyl)-7-chloro-1,2,3,4-tetrahydro-4-oxo-2-quinazolinyl]phenoxy]-1-[[(3-hydroxy-3-oxopropyl)ethylamino]carbonyl]-L-proline | 100 mg. |
| Magnesium stearate | 7 mg. |
| Lactose | 193 mg. |
| | 300 mg. |

In a similar manner, capsules containing 100 mg. of the product of any of Examples 1 to 11 and 13 to 40 can be prepared.

EXAMPLE 43

An injectable solution is prepared as follows:

| | |
|---|---|
| [1(S),4S]-4-[4-[6-(Amino-sulfonyl)-7-chloro-1,2,3,4-tetrahydro-4-oxo-2-quinazolinyl]phenoxy]-1-[3-(benzoylthio)-2-methyl-1-oxopropyl]-L-proline | 500 g. |
| Methyl paraben | 5 g. |
| Propyl paraben | 1 g. |
| Sodium chloride | 25 g. |
| water for injection | 5 l. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 1 to 3 and 5 to 40.

What is claimed is:

1. A compound of the formula

[structural formula with $R_{14}$, $N$, $Z$, $R_1$, $A_1$, $A_2$, $R_2$, $X$, $A-N$, $COOR$, $(L)$, $H$]

and a physiologically acceptable salt thereof wherein

X is oxygen or sulfur;

$-A_1-A_2-$ is $-CH-NH-$ or $-C=N-$;

A is $$R_4-S-CH_2-\underset{R_3}{CH}-\underset{O}{\overset{\|}{C}}-,\ R_8OOC-(CH_2)_2-\underset{R_7}{N}-\underset{O}{\overset{\|}{C}}-,$$

$$R_9OOC-\underset{R_{10}}{CH}-NH-\underset{R_{11}}{CH}-\underset{O}{\overset{\|}{C}}-,\ \text{or}\ R_{12}-\underset{OR_{13}}{\overset{\overset{O}{\|}}{P}}-CH_2-\underset{O}{\overset{\|}{C}}-;$$

R, $R_8$ and $R_9$ are independently selected from the group consisting of hydrogen, lower alkyl, benzyl, benzhydryl, and a physiologically acceptable salt forming ion;

$R_1$ and $R_2$ are independently selected from the group consisting of hydrogen, halogen, lower alkyl, lower alkoxy, halo substituted lower alkyl, nitro, and $-SO_2NH_2$;

Z is $$-\overset{\overset{O}{\|}}{C}-;$$

$R_3$ is hydrogen, lower alkyl, halo substituted lower alkyl, phenyl, benzyl, phenethyl or cycloalkyl wherein cycloalkyl is a saturated ring of 3 to 7 carbons;

$R_4$ is hydrogen or $$R_5-\overset{\overset{O}{\|}}{C}-;$$

$R_5$ is lower alkyl,

[structural formulas: phenyl-$(CH_2)_n-$ with $R_6$, thiophene-$(CH_2)_n-$, furan-$(CH_2)_n-$, or pyridine-$(CH_2)_n-$]

n is zero, one, two, three or four;

$R_6$ is hydrogen, lower alkyl, lower alkoxy, halogen, or hydroxy;

$R_7$ is lower alkyl or cycloalkyl wherein cycloalkyl is a saturated ring of 3 to 7 carbons;

$R_{10}$ is hydrogen, lower alkyl,

[structural formula: phenyl-$(CH_2)_n-$ with $R_6$], halo substituted lower alkyl, hydroxy substituted lower alkyl, $-(CH_2)_q$-cycloalkyl wherein cycloalkyl is a saturated ring of 3 to 7 carbons, $-(CH_2)_q$-N(lower alkyl)$_2$, $-(CH_2)_q$-NH$_2$, $-(CH_2)_q$-carboxy, $-(CH_2)_q$-SH, $-(CH_2)_q$-S-lower alkyl,

[structural formulas: $-(CH_2)_q$-phenyl-OH with OH, $-(CH_2)_q$-indolyl]

$-(CH_2)_q$-pyrrolyl-N, $-(CH_2)_q$-guanidinyl, $-(CH_2)_q-\overset{\overset{O}{\|}}{C}-NH_2$, [structural formula with $-CH$, $CH_2$-phenyl-$R_6$, $NH-C(=O)$-phenyl-$R_6$];

q is one, two, three or four;

$R_{11}$ is hydrogen, lower alkyl, halo substituted lower alkyl, hydroxy substituted lower alkyl, $-(CH_2)_q$-NH$_2$, $-(CH_2)_q$-N(lower alkyl)$_2$, $-(CH_2)_q$-guanidinyl,

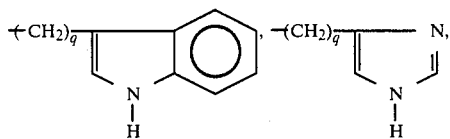

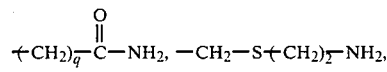

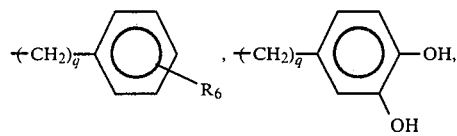

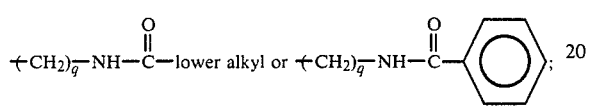

$R_{12}$ is alkyl of 1 to 10 carbons,

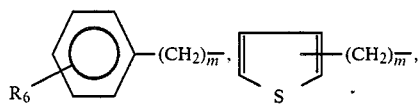

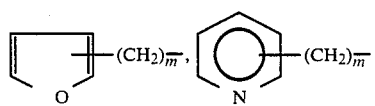

cycloalkyl-$(CH_2)_m$- wherein cycloalkyl is a saturated ring of 3 to 7 carbons;

m is zero or an integer from 1 to 7;

$R_{13}$ is hydrogen, lower alkyl, benzyl, benzhydryl, a physiologically acceptable salt forming ion or

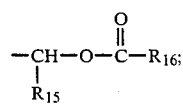

$R_{15}$ is hydrogen, lower alkyl, cycloalkyl wherein cycloalkyl is a saturated ring of 3 to 7 carbons, or phenyl;

$R_{16}$ is hydrogen, lower alkyl, lower alkoxy, cycloalkyl wherein cycloalkyl is a saturated ring of 3 to 7 carbons, phenyl, benzyl, or phenethyl; and $R_{14}$ is hydrogen, lower alkyl, cycloalkyl-$(CH_2)_n$— wherein cycloalkyl is a saturated ring of 3 to 7 carbons,

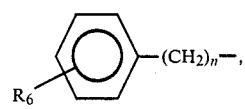

halo substituted lower alkyl, hydroxy substituted lower alkyl, —$(CH_2)_q$-N(lower alkyl)$_2$, or —$(CH_2)_q$-NH$_2$.

2. A compound of claim 1 of the formula

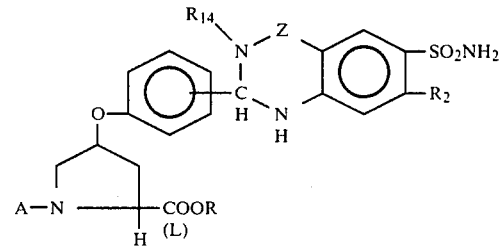

and a pharmaceutically acceptable salt thereof wherein

R is hydrogen, lower alkyl of 1 to 4 carbons, or an alkali metal salt ion;

$R_{14}$ is hydrogen or lower alkyl of 1 to 4 carbons;

$R_2$ is halogen, lower alkyl of 1 to 4 carbons, or halo substituted lower alkyl of 1 to 4 carbons;

$R_4$ is hydrogen or

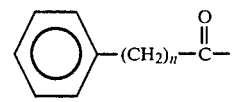

wherein n is zero, one or two;

$R_3$ is lower alkyl of 1 to 4 carbons;

$R_8$ is hydrogen, lower alkyl of 1 to 4 carbons, or an alkali metal salt ion;

$R_7$ is lower alkyl of 1 to 4 carbons;

$R_9$ is hydrogen, lower alkyl of 1 to 4 carbons, or an alkali metal salt ion;

$R_{10}$ is

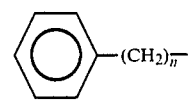

wherein n is zero, one, two, three or four;

$R_{11}$ is lower alkyl of 1 to 4 carbons, —$CH_2$-S-$(CH_2)_2$-$NH_2$, or —$(CH_2)_4$-$NH_2$;

$R_{12}$ is alkyl of 1 to 10 carbons or

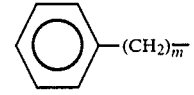

wherein m is zero or an integer from 1 to 7;

$R_{13}$ is hydrogen, alkali metal salt ion or

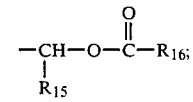

$R_{15}$ is hydrogen, straight or branched chain lower alkyl of 1 to 4 carbons, or cyclohexyl; and $R_{16}$ is straight or branched chain lower alkyl of 1 to 4 carbons.

3. A compound of claim 2 wherein

A is

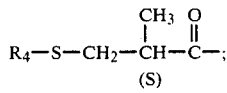

R$_{14}$ is hydrogen or methyl;
R$_2$ is chloro or trifluoromethyl; and
R$_4$ is hydrogen or

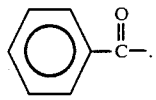

4. The compound of claim 3, [1(S),4S]-4-[3-[6-(aminosulfonyl)-7-chloro-1,2,3,4-tetrahydro-4-oxo-2-quinazolinyl]phenoxy]-1-(3-mercapto-2-methyl-1-oxopropyl)-L-proline.

5. The compound of claim 3, [1(S),4S]-4-[2-[6-(aminosulfonyl)-7-chloro-1,2,3,4-tetrahydro-4-oxo-2-quinazolinyl]phenoxy]-1-(3-mercapto-2-methyl-1-oxopropyl)-L-proline.

6. The compound of claim 3, [1(S),4S]-4-[4-[6-(aminosulfonyl)-7-chloro-1,2,3,4-tetrahydro-4-oxo-2-quinazolinyl]phenoxy]-1-(3-mercapto-2-methyl-1-oxopropyl)-L-proline.

7. The compound of claim 3, [1(S),4S]-4-[4-[6-(aminosulfonyl)-7-chloro-1,2,3,4-tetrahydro-4-oxo-2-quinazolinyl]phenoxy]-1-[3-(benzoylthio)-2-methyl-1-oxopropyl]-L-proline.

8. The compound of claim 3, [1(S),4S]-4-[3-[6-(aminosulfonyl)-7-chloro-1,2,3,4-tetrahydro-4-oxo-2-quinazolinyl]phenoxy]-1-[3-(benzoylthio)-2-methyl-1-oxopropyl]-L-proline.

9. The compound of claim 3, [1(S),4S]-4-[2-[6-(aminosulfonyl)-7-chloro-1,2,3,4-tetrahydro-4-oxo-2-quinazolinyl]phenoxy]-1-[3-(benzoylthio)-2-methyl-1-oxopropyl]-L-proline.

10. A compound of claim 2 wherein A is

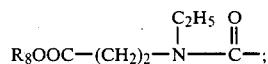

R$_{14}$ is hydrogen or methyl;
R$_2$ is chloro or trifluoromethyl; and
R$_8$ is hydrogen, ethyl, or an alkali metal salt ion.

11. The compound of claim 10, (cis)-4-[3-[6-(aminosulfonyl)-7-chloro-1,2,3,4-tetrahydro-4-oxo-2-quinazolinyl]phenoxy]-1-[[(3-ethoxy-3-oxopropyl)ethylamino]carbonyl]-L-proline.

12. The compound of claim 10, (cis)-4-[3-[6-(aminosulfonyl)-7-chloro-1,2,3,4-tetrahydro-4-oxo-2-quinazolinyl]phenoxy]-1-[[(3-hydroxy-3-oxopropyl)ethylamino]carbonyl]-L-proline.

13. A compound of claim 2 wherein A is

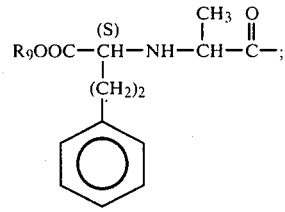

R$_{14}$ is hydrogen or methyl; and
R$_9$ is hydrogen, ethyl, or an alkali metal salt ion.

14. A compound of claim 2 wherein A is

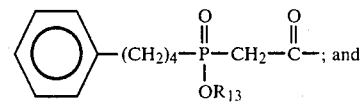

R$_{14}$ is hydrogen or methyl.

15. A composition useful for treating hypertension comprising a pharmaceutically acceptable carrier and a hypotensive agent or pharmaceutically acceptable salt thereof of the formula

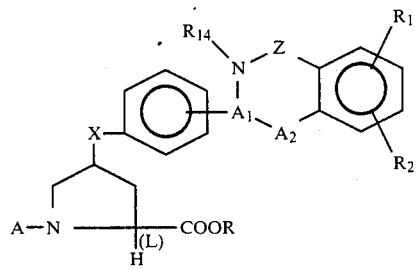

wherein A, —A$_1$—A$_2$—, R, R$_1$, R$_2$, R$_{14}$, X and Z are as defined in claim 1.

16. The method of alleviating hypertension in a mammalian species which comprises administering an effective amount of the composition of claim 15.

17. A compound of the formula

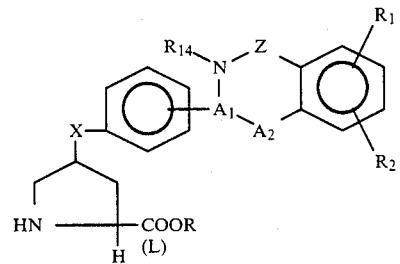

wherein —A$_1$—A$_2$—, R$_1$, R$_2$, R$_{14}$, X and Z are as defined in claim 1.

* * * * *